United States Patent [19]
Pierschbacher et al.

[11] Patent Number: 6,013,625
[45] Date of Patent: *Jan. 11, 2000

[54] METHOD AND COMPOSITION FOR TREATING THROMBOSIS

[75] Inventors: Michael D. Pierschbacher, San Diego; David S. Lukeman, Oceanside; Soan Cheng; William S. Craig, both of San Diego, all of Calif.

[73] Assignee: La Jolla Cancer Research Foundation, San Diego, Calif.

[*] Notice: This patent is subject to a terminal disclaimer.

[21] Appl. No.: 08/322,409

[22] Filed: Oct. 12, 1994

Related U.S. Application Data

[63] Continuation of application No. 08/193,903, Feb. 9, 1994, abandoned, which is a continuation of application No. 08/032,449, Mar. 16, 1993, abandoned, which is a continuation of application No. 07/860,117, Mar. 30, 1992, abandoned, which is a continuation of application No. 07/506,444, Apr. 6, 1990, abandoned.

[51] Int. Cl.⁷ .................................................. A61K 38/00
[52] U.S. Cl. .............................. 514/9; 514/11; 530/317; 530/402
[58] Field of Search .................................. 530/317, 324, 530/325, 326, 327, 328, 329, 330; 514/11, 12, 13, 14, 15, 16, 17, 18, 9

[56] References Cited

U.S. PATENT DOCUMENTS

| | | |
|---|---|---|
| 4,517,666 | 5/1985 | Hideo . |
| 4,547,489 | 10/1985 | Goldstein . |
| 4,578,079 | 3/1986 | Ruoslahit et al. ........................ 530/330 |
| 4,589,881 | 5/1986 | Pierschbacher et al. ................. 530/350 |
| 4,605,512 | 8/1986 | Schaller et al. . |
| 4,614,517 | 9/1986 | Ruoslahti ............................... 530/300 |
| 4,661,111 | 4/1987 | Ruoslahti et al. ........................ 530/350 |
| 4,683,291 | 7/1987 | Zimmerman et al. ..................... 530/324 |
| 4,789,734 | 12/1988 | Pierschbacher ....................... 530/350 X |
| 4,792,525 | 12/1988 | Ruoslahti . |
| 4,857,508 | 8/1989 | Adams et al. ............................. 514/18 |
| 4,879,313 | 11/1989 | Tjoeng et al. . |
| 4,929,601 | 5/1990 | Brunetti et al. ........................... 514/18 |
| 4,943,562 | 7/1990 | Jolles et al. .............................. 514/18 |
| 5,023,233 | 6/1991 | Nutt et al. ................................. 514/11 |
| 5,037,808 | 8/1991 | Adams et al. . |
| 5,041,380 | 8/1991 | Ruoslahti . |
| 5,066,592 | 11/1991 | Huang et al. . |
| 5,612,311 | 3/1997 | Pierschbacher et al. ................. 514/11 |
| 5,643,872 | 7/1997 | Ali et al. . |
| 5,648,330 | 7/1997 | Pierschbacher et al. ................. 514/11 |
| 5,672,585 | 9/1997 | Pierschbacher et al. ................. 514/11 |

FOREIGN PATENT DOCUMENTS

| | | |
|---|---|---|
| 317053 | 5/1988 | European Pat. Off. . |
| 0275478 | 7/1988 | European Pat. Off. ................. 530/330 |
| 0275748 | 7/1988 | European Pat. Off. ................. 530/317 |
| 0406428 A1 | 8/1989 | European Pat. Off. ........... C07K 7/06 |
| 338634 | 10/1989 | European Pat. Off. . |
| 0341915 | 11/1989 | European Pat. Off. ................. 514/16 |
| 368486 | 5/1990 | European Pat. Off. . |
| 3841763A1 | 6/1990 | Germany . |
| 2207922 | 2/1989 | United Kingdom . |
| WO 89/00200 | 1/1989 | WIPO . |
| WO 89/04837 | 6/1989 | WIPO . |
| WO 89/05150 | 7/1989 | WIPO ................................... 530/317 |
| WO 89/07609 | 8/1989 | WIPO . |
| WO 90/00178 | 1/1990 | WIPO . |
| WO 90/02751 | 3/1990 | WIPO . |
| WO 90/11297 | 4/1990 | WIPO . |
| WO 90/06943 | 6/1990 | WIPO . |
| WO 90/15620 | 12/1990 | WIPO . |
| WO 91/01331 | 2/1991 | WIPO . |
| WO 91/15515 | 10/1991 | WIPO . |
| WO 91/15516 | 10/1991 | WIPO . |
| WO 92/17492 | 10/1992 | WIPO . |

OTHER PUBLICATIONS

Kopple et al., "Conformations of Arg–Gly–Asp Containing Heterodetic Cyclic Peptides: Solution and Crystal Studies", J. Am. Chem. Soc., 114: 9615–9623, (1992).
Gougos and Letarte, "Primary Structure of Endoglin, an RDG-containing Glycoprotein of Human Endothelial Cells", J. Biol. Chem., 265(15):8361–8364 (1990).
Wright et al., C3bi receptor (complement receptor type 3) recognizes a region of complement protein C3 containing the sequence Arg–Gly–Asp, PNAS, USA, 84:1965–1968 (1987).
Gehlsen et al., J. Cell. Biol. 106:925–930 (1988).
Gehlsen et al., J. Cell. Biol. 105:3097–3104 (1987).
Siebers et al., Eur. J. Biochem. 178:131–140 (1988).
Ruoslahti et al., Cell 44:517–518 (1986).
Ruoslahti et al., Falk Symposium 43:239–244 (1987).
Bodanszky, Principles of Peptide Synthesis 217–222 (1984).
Marx, Science 248:1491–1493 (1990).
Creighton, Proteins 9 (1984).
Dayhoff, Atlas of Protein Sequences and Structure 5:89–99 (1972).
Joubert et al., Biochim. Biophys. Acta. 579:228–233 (1979).
Gan et al., J. Biol. Chem. 263(36):19827–19832 (1988).
Huang et al., J. Biol. Chem. 262(33):16157–16163 (1987).
Pelton et al., Proc. Natl. Acad. Sci. USA 82:236–239 (1985).
Sakakibara et al., BBA 303:198–202 (1973).
Kaiser and Kezcy, Science 223:249–255 (1984).
Ohsaku et al., Int. J. Biol. Macromol. 6:234–240 (1984).
Cheresh, Chem. Abstract 104, abstract No. 183980c (1986).
Yamada, Chem. Abstract 107, abstract No. 5066p (1987).
Poole, Chem. Abstract 105, abstract No. 169400c (1986).
Toda et al., J. Cell. Biol. 105:3097–3104 (1987).
Singer et al., J. Cell. Biol. 104:573–584 (1987).
Lash et al., Dev. Biol. 123:411–420 (1987).

(List continued on next page.)

Primary Examiner—Cecilia J. Tsang
Assistant Examiner—Patrick R. Delaney
Attorney, Agent, or Firm—Campbell & Flores, LLP

[57] ABSTRACT

The invention provides RGD containing peptides which are cyclized and contain hydrophobic moieties adjacent the carboxy terminus of the RGD sequence. Such peptides have an high affinity for the receptor IIb/IIIa and low affinity for the fibronectin and vitronectin receptors. Such peptides can be administered in a suitable physiologically acceptable carrier to therapeutically treat thrombosis.

12 Claims, 12 Drawing Sheets

OTHER PUBLICATIONS

Pierschbacher and Ruoslahti, J. Biol. Chem. 262:17294–17298 (1987).
Haverstick et al., Blood 66:946–952 (1985).
Ruggeri et al., Proc. Natl. Acad. Sci. USA 83:5708–5712 (1986).
Ginsberg et al., J. Biol. Chem. 260:3931–3936 (1985).
Pierschbacher et al., Proc. Natl. Acad. Sci. USA 81:5985–5988 (1984).
Kloczewisk et al., Biochemistry 23:1767–1774 (1984).
Gartner and Bennett, J. Biol. Chem. 260:11891–11894 (1985).
Kleffer and Phillips, Annu. Rev. Cell Biol. 36:329–357 (1990).
Plow et al., Proc. Natl. Acad. Sci. USA 82:8057–8061 (1985).
Pytela et al., Proc. Natl. Acad. Sci. USA 82:5766–5770 (1985).
Pytela et al., Cell 40:191–198 (1985).
Pytela et al., Science 231:1559–1562 (1985).
Gardner et al, Cell 42:439–448 (1985).
Pierschbacher et al., Nature 309:30–33 (1984).
D'Souza et al., J. Biol. Chem. 263:3943–3951 (1988).
Parise et al., J. Biol. Chem. 262:12597–12602 (1987).
Haskei et al., Thromb. Res. 56:687–695 (1988).
Plow et al., Blood 70:110–115 (1987).
Ruoslahti et al., J. Clin. Invest. 87:1–5 (1991).
Ali et al., Peptides Proc. 11th Amer. Peptide Symposium, La Jolla, CA, Marshall & Rivier, eds. (Jul. 9–14, 1989).
Garsky et al., Proc. Natl. Acad. Sci. USA 86:4022–4026 (1989).
Dennis et al., Proc. Natl. Acad. Sci. USA 87:2471–2475 (1989).
Chao et al., Proc. Natl. Acad. Sci. USA 86:8050–8054 (1989).
Shebuski et al., J. Biol. Chem. 264:21550–21556 (1989).
Huang et al., Biochemistry 28:661–666 (1989).
Spatola and Krzysztof, Tetrahedron 44(3):821–833 (1988).
Garo and Spatola, Biochem. Biophys. Res. Commun. 120(3):840–845 (1984).
Edwards and Spatola, Biochem. Biophys. Res. Commun. 136(2):730–736 (1986).
Spatola and Edwards, Biopolymers 25:s229–s244 (1986).
Davies et al., Biochem. Soc. Trans. 18:11326–11328 (1990).
Drickamer et al., J. Biol. Chem. 261:6878–6887 (1986).
Rauvala et al., J. Cell. Biol. 107:2293–2305 (1988).
Maes et al., Fed. Europ. Biochem. Soc. 241:41–45 (1988).
Moos et al., Nature 334:701–703 (1988).
Neurath et al., Mol. Immun. 27:539–549 (1990).
Kirchofer et al., J. Biol. Chem. 265:18525–18530 (1990).
Ratner et al., Nature 313:277–284 (1985).
Bond et al., Biochemistry 28:6110–6113 (1989).
Ohlstein et al., Thromb. Res. 46:576–585 (1987).
Harvey, J. Toxicol.—Toxin Reviews 3:91–137 (1984).
Dufton, CRC Crit. Rev. in Biochem. 14:113–171 (1983).
Olson, Nature 228:438–442 (1970).
Pelton, J. Med. Chem. 29:2370–2375 (1986).
Lebl, Collection Czechosloval Chem. Commun. 49:2680–2688 (1984).
Stanfield, J. Org. Chem. 51:5153–5156 (1986).
Barker, Protein Society 2nd Symposium (1987).
Pilrenbaumer, Chem Abstract #112:199131 of WO89/05150, Jun. 15, 1989.
Gehlsen et al., "Inhibition of In Vitro Tumor Cell Invasion by Arg–Gly–Asp–containing Synthetic Peptides" J. Cell. Biol. 106:925–930 (1988).
Siebers et al., "The $K^+$–translocating Kdp–ATPase from *Escherichia coli*, Purification, enzymatic properties and production of complex– and subunit–specific antisera" Eur. J. Biochem. 178:131–140 (1988).
Ruoslahti et al., "Arg–Gly–Asp: A Versatile Cell Recognition Signal" Cell 44:517–518 (1986).
Ruoslahti et al., "Arg–Gly–Asp: a cellular recognition system for positional signalling" Falk Symposium 43:239–244 (1987).
Bodansky, Principles of Peptide Synthesis 217–222 (1984).
Marx, "Holding the Line Against Heart Disease" Science 248:1491–1493 (1990).
Creighton, Proteins, Structures and Molecular Principles, Chapter 9, W.H. Freeman and Company, New York (1984).
Dayhoff et al., Chapter 9: "A Model of Evolutionary Change in Proteins", in Atlas of Protein Sequences and Structure 5:89–99 (1972).
Joubert et al., " Some Properties and the Complete Primary Structures of Two Reduced and S–Carboxymethylated Polypeptides (S5C1 and S5C10) From Dendroaspis Jamesoni Kaimosae (Jameson's Mamba) Venom" Biochim. Biophys. Acta. 579:228–233 (1979).
Gan et al., " Echistatin, A Potent Platelet Aggregation Inhibitor from the Venom of the Viper, Echis Carinatus" J. Biol. Chem. 263(36):19827–19832 (1988).
Huang et al., "Trigramin, A Low Molecular Weight Peptide Inhibiting Fibrinogen Interaction with Platelet Receptors Expressed on Glycoprotein IIb–IIIa Complex" J. Biol. Chem. 262(33):16157–16163 (1987).
Pelton et al., "Conformationally restricted analogs of somatostatin with high $\mu$–opiate receptor specificity" Proc. Natl. Acad. Sci. USA 82:236–239 (1985).
Sakakibara et al., "Synthesis of (Pro–Hyp–Gly)n of defined molecular weights , Evidence for the stabilization of collagen triple helix by hydroxypyroline" BBA Report 303:198–202 (1973).
Kaiser and Kezcy, "Amphiphilic Secondary Structure: Design of Peptide Hormones" Science 223:249–255 (1984).
Ohsaku et al., "Electronic structures of collagen model polymers: (Gly–Pro)n, (Gly–Hyp)n, (Ala–Pro)n, (Ala–Hyp)n, (Gly–Pro–Gly)n, (Gly–Hyp–Gly)n, (Gly–Pro–Pro)n, and (Gly–Pro–Hyp)n" Int. J. Biol. Macromol. 6:234–240 (1984).
Cheresh, "Disialogangliosides GD2 and GD3 are involved in the attachment of human melanoma and neuroblastoma cells to extracellular matrix proteins" Chem. Abstract 104, abstract No. 183980c (1986).
Yamada, "Peptide inhibitors of fibronectin, laminin, and other adhesion molecules: unique and shared features" Chem. Abstract 107, abstract No. 5066p (1987).
Poole, Chem. Abstract 105, abstract No. 169400c (1986).
Toda et al., "Fibronectin Receptors of Human Keratinocytes and Their Expression during Cell Culture" J. Cell. Biol. 105:3097–3104 (1987).
Singer et al., "The Fibronectin Cell Attachment Sequence Arg–Gly–Asp–Ser Promotes Focal Contact Formation during Early Fibroblast Attachment and Spreading" J. Cell. Biol. 104:573–584 (1987).
Lash et al., "Synthetic Peptides That Mimic the Adhesive Recognition Signal of Fibronectin: Differential Effects on Cell–Cell and Cell–Substratum Adhesion in Embryonic Chick Cells" Dev. Biol. 123:411–420 (1987).

Pierschbacher and Ruoslahti, "Influence of Stereochemistry of the Sequence Arg–Gly–Asp–Xaa on Binding Specificity in Cell Adhesion" J. Biol. Chem. 262:17294–17298 (1987).

Haverstick et al., "Inhibition of Platelet Adhesion to Fibronectin, Fibrinogen, and von Willebrand Factor Substrates by a Synthetic Tetrapeptide Derived From the Cell Binding Domain of Fibronectin" Blood 66:946–952 (1985).

Ginsberg et al., "Inhibition of Fibronectin Binding to Platelets by Proteolytic Fragments and Synthetic Peptides Which Support Fibroblast Adhesion*" J. Biol. Chem. 260:3931–3936 (1985).

Pierschbacher et al., "Variants of the cell recognition site of fibronectin that retain attachment–promoting activity" Proc. Natl. Acad. Sci. USA 81:5985–5988 (1984).

Kloczewisk et al., "Platelet Receptor Recognition Site on Human Fibrinogen. Synthesis and Structure–Function Relationship of Peptides Corresponding to the Carboxy–Terminal Segment of the Gamman Chain" Biochemistry 23:1767–1774 (1984).

Gartner and Bennett, "The Tetrapeptide Analogue of the Cell Attachment Site of Fibronectin Inhibits Platelet Aggregation and Fibrinogen Binding to Activated Platelets" J. Biol. Chem. 260:11891–11894 (1985).

Kleffer and Phillips, "Platelet Membrane Glycoproteins: Functions in Cellular Interactions" Annu. Rev. Cell Biol. 36:329–357 (1990).

Plow et al., "The effect of Arg–Gly–Asp–containing peptides on fibrinogen and von Willebrand factor binding to platelets" Proc. Natl. Acad. Sci. USA 82:8057–8061 (1985).

Pytela et al., "A 125/115–kDa cell surface receptor specific for vitronectin interacts with the arginine–glycine–aspartic acid adhesion sequence derived from fibronectin" Proc. Natl. Acad. Sci. USA 82:5766–5770 (1985).

Pytela et al., "Identification and Isolation of a 140kd Cell Surface Glycoprotein with Properties Expected of a Fibronectin Receptor" Cell 40:191–198 (1985).

Pytela et al., "Platelet Membrane Glycoprotein IIb/IIIa: Member of a Family of Arg–Gly–Asp–Specific Adhesion Receptors" Science 231:1559–1562 (1986).

Gardner et al, "Interaction of Fibronectin with its Receptor on Platelets" Cell 42:439–448 (1985).

Pierschbacher et al., "Cell attachment activity of fibronectin can be duplicated by small synthetic fragments of the molecule" Nature 309:30–33 (1984).

D'Souza et al., "Chemical Cross–linking of Arginyl–Glycyl–Aspartic Acid Peptides to an Adhesion Receptor on Platelets" J. Biol. Chem. 263:3943–3951 (1988).

Parise et al., "Synthetic Peptides Derived from Fibrinogen and Fibronectin Change the Conformation of Purified Platelet Glycoprotein IIb–IIIa" J. Biol. Chem. 262:12597–12602 (1987).

Haskel et al., "Deaggregation of Human Platelets in Vitro by an RGD Analog Antagonist of Platelet Glycoprotein IIb/IIIa Receptors" Thromb. Res. 56:687–695 (1988).

Plow et al., "Arginyl–Glycyl–Aspartic Acid Sequences and Fibrinogen Binding to Platelets" Blood 70:110–115 (1987).

Ruoslahti et al., "Integrins" J. Clin. Invest. 87:1–5 (1991).

Ali et al., Peptides Proc. 11th Amer. Peptide Symposium, La Jolla, CA, Marshall & Rivier, eds. (Jul. 9–14, 1989).

Garsky et al., "Chemical synthesis of echistatin, a potent inhibitor of platelet aggregation from *Echis carinatus*: Synthesis and biological activity of selected analogs" Proc. Natl. Acad. Sci. USA 86:4022–4026 (1989).

Dennis et al., "Platelet glycoprotein IIb–IIIa protein antagonists from snake venoms: Evidence for a family of platelet–aggregation inhibitors" Proc. Natl. Acad. Sci. USA 87:2471–2475 (1989).

Chao et al., "*Agkistrodon piscivorus piscivorus* platelet aggregation inhibitor: A potent inhibitor of platelet activation" Proc. Natl. Acad. Sci. USA 86:8050–8054 (1989).

Shebuski et al., "Characterization and Platelet Inhibitory Activity of Bitistatin, a Potent Arginine–Glycine–Aspartic Acid–containing Peptide from the Venom of the *Viper Bitis arientans**" J. Biol. Chem. 264:21550–21556 (1989).

Huang et al., "Trigramin: Primary Structure and Its Inhibition of von Willebrand Factor Binding to Glycoprotein IIb/IIIa Complex on Human Platelets" Biochemistry 28:661–666 (1989).

Spatola and Krzysztof, "Amide Bond Surrogates: Pseudopeptides and Macrocycles" Tetrahedron 44(3):821–833 (1988).

Gero and Spatola, "Synthesis and Biological Activity of a Cyclic Pseudohexapeptide Analog of Somatostatin" Biochem. Biophys. Res. Commun. 120(3):840–845 (1984).

Edwards and Spatola, "In Vitro Activity Profiles of Cyclic and Linear Enkephalin Pseudopeptide Analogs" Biochem. Biophys. Res. Commun. 136(2):730–736 (1986).

Spatola and Edwards, "Synthesis, Characterization, and Structural Properties of Linear and Cyclic Enkephalin Pseudopeptide Diastereomers*" Biopolymers 25:S229–S244 (1986).

Drickamer et al., "Mannose–binding Proteins Isolated from Rat Liver Contain Carbohydrate–recognition Domains Linked to Collagenous Tails" J. Biol. Chem. 261:6878–6887 (1986).

Rauvala et al., "The Adhesive and Neurite–promoting Molecule p30: Analysis of the Amino–Terminal Sequence and Production of Antipeptide Antibodies that Detect p30 at the Surface of Neuroblastoma Cells and of Brain Neurons" J. Cell. Biol. 107:2293–2305 (1988).

Maes et al., "The complete amino acid sequence of bovine milk angiogenin" Fed. Europ. Biochem. Soc. 241:41–45 (1988).

Moos et al., "Neural adhesion molecule L1 as a member of the immunoglobulin superfamily with binding domains similar to fibronectin" Nature 334:701–703 (1988).

Neurath et al., "Confronting the Hypervariability of an Immunodominant Epitope Eliciting Virus Neutralizing Antibodies from the Envelope Glycoprotein of the Human Immunodeficiency Virus Type 1 (HIV–1)" Mol. Immun. 27:539–549 (1990).

Kirchhofer et al., "Cation–dependent Changes in the Binding Specificity of the Platelet Receptor GPIIb/IIIa" J. Biol. Chem. 265:18525–18530 (1990).

Ratner et al., "Complete nucleotide sequence of the AIDS virus, HTLV–III" Nature 313:277–284 (1985).

Bond et al., "Amino Acid Sequence of Bovine Angiogenin" Biochemistry 28:6110–6113 (1989).

Ohlstein et al., "Tissue–type Plasminogen Activator and Streptokinase Induce Platelet Hyperaggregability in the Rabbit" Thromb. Res. 46:575–585 (1987).

Harvey et al., "Toxins from Mamba Venoma that Facilitate Neuromuscular Transmission" in J. Toxicol.—Toxin Reviews 3:91–137 (1984).

Dufton and Hider, "Conformational Properties of the Neurotoxins and Cytotoxins Isolated from Elapid Snake Venoms" in CRC Crit. Rev. in Biochem. 14:113–171 (1983).

Olson et al., "Primary Structure of α–Lytic Protease: a Bacterial Homologue of the Pancreatic Serine Proteases" Nature 228:438–442 (1970).

Pelton, "Design and Synthesis of Conformationally Constrained Somatostatin Analogues with High Potency and Specificity for μ Opioid Receptors" J. Med. Chem. 29:2370–2375 (1986).

Lebl et al., "Modification of the Disulfide Bridge in Cyclic Melanotropins" Collection Czechosloval Chem. Commun. 49:2680–2688 (1984).

Stanfield et al., "Preparation of β9β–Dialkyl Analogues of Cysteine Suitable for Peptide Synthesis" J. Org. Chem. 51:5153–5156 (1986).

Ruggeri et al., "Inhibition of platelet function with synthetic peptides designed to be high–affinity antagonists of fibrinogen binding to platelets" Proc. Natl. Acad. Sci. USA 83:5708–5712 (1986).

Davies et al., "Synthetic peptide mimics of the active domain of fibronectin" Biochem. Soc. Trans. 18:1326–1328 (1990).

Barker et al., "Synthesis of Cyclic Hexapeptides Containing the Arg–Gly–Asp–Val Sequence as Potential Inhibitors of Fibronectin Mediated Cell Adhesion" Protein Society 2nd Symposium (1987).

Creighton, T., *Proteins*, W.H. Freeman & Co., p. 9, 1984.

Marx, J., *Science*, 248:1491–1493, Jun. 1990.

Huang, T. et al., *Journal of Biological Chemistry*, 262(33):16157–16163, Nov. 1987.

Toda, K., et al., *Journal of Cell Biology*, 105 (No. 6, Pt 2): 3097–3104, Dec. 1987.

Gehlsen, K., et al., *Journal of Cell Biology*, 106:925–930, Mar. 1988.

Lash, J., et al., *Developmental Biology*, 123: 411–420, 1987.

Pierschbacher, M., et al., *Journal of Biological Chemistry*, 262(36):17294–17298, 1987.

Dayoff, M., *Atlas of Protein Sequence and Structure*, vol. 5, pp. 89–99, 1972.

Jowbert, F. et al., *Bochimca et Biophysica Acta*, 579:228–233, 1979.

Gan, Z., et al., *Journal of Biological Chemistry*, 263(36):19827–19823, Dec. 25, 1988.

Haverstick, D, et al., *Blood*, 66(4):946–952, 1985.

Singer, I., et al., *Journal of Cell Biology*, 104:573–584, 1987.

PEPTIDE PREVENTION OF CORONARY THROMBOSIS

| TREATMENT | TIME FULL OCCLUSION (min)[a] |
|---|---|
| Control | 136 ± 15 (13) |
| Analogue 2G | |
| 10 mg/kg | 127 ± 41 (3) |
| Analogue 4Q | |
| 5 mg/kg | 165 ± 10 (2)[b] |
| 5 mg/kg (Low platelet count) | >300 (2) |
| 10 mg/kg | >300 (1)[c] |
| Analogue 4R | |
| 3 mg/kg | 95 (1) |
| 10 mg/kg | >300 (1)[c] |

[a] values are mean ± SEM for the number of determinations that appears in parentheses.

Statistical significance vs. control denoted as follows:

Effects of RGD Peptides on Hemodynamic Parameters

| Treatment | Mean Arterial Pressure (mm Hg) | Heart Rate (Beats/Min) | Platelet Count ($10^3$/ml) | Bleeding Time (Min) |
|---|---|---|---|---|
| ANALOGUE 2G | | | | |
| (10 mg/kg) (N-3) | | | | |
| Baseline | 104±5 | 160±10 | 480±12 | 2.9±0.6 |
| 1 hr. | 96±7 | 172±8 | 409±19 | 2.8±0.3 |
| 3 hr. | ND | ND | 395±36 | 2.6±0.1 |
| 5 hr. | ND | ND | 556±16 | 2.6±0.1 |
| ANALOGUE 4Q | | | | |
| (5 mg/kg) (N-2) | | | | |
| Baseline | 103±3 | 158±9 | 316±52 | 2.8±0.3 |
| 1 hr. | 107±6 | 160±10 | 406±185 | 2.6±0.1 |
| 3 hr. | 110±10 | 168±7 | 375±25 | 3.6±0.1 |
| 5 hr. | ND | ND | 355±47 | 3.0±0.5 |
| (10 mg/kg) (N-1) | | | | |
| Baseline | 100 | 162 | 307 | 4.0 |
| 1 hr. | 104 | 170 | 420 | 7.5 |
| 3 hr. | 105 | 160 | 379 | 5.5 |
| 5 hr. | 107 | 165 | 290 | 5.5 |
| ANALOGUE 4R | | | | |
| (3 mg/kg) (N-1) | | | | |
| Baseline | 103 | 170 | 393 | 4.0 |
| 1 hr. | 110 | 165 | 367 | 4.0 |
| 3 hr. | ND | ND | 420 | 4.0 |
| 5 hr. | ND | ND | 575 | 5.0 |
| (10 mg/kg) (N-1) | | | | |
| Baseline | 100 | 162 | 512 | 4.0 |
| 1 hr. | 95 | 168 | 513 | 5.0 |
| 3 hr. | 102 | 172 | 491 | 5.0 |
| 5 hr. | 107 | 170 | 460 | 5.0 |

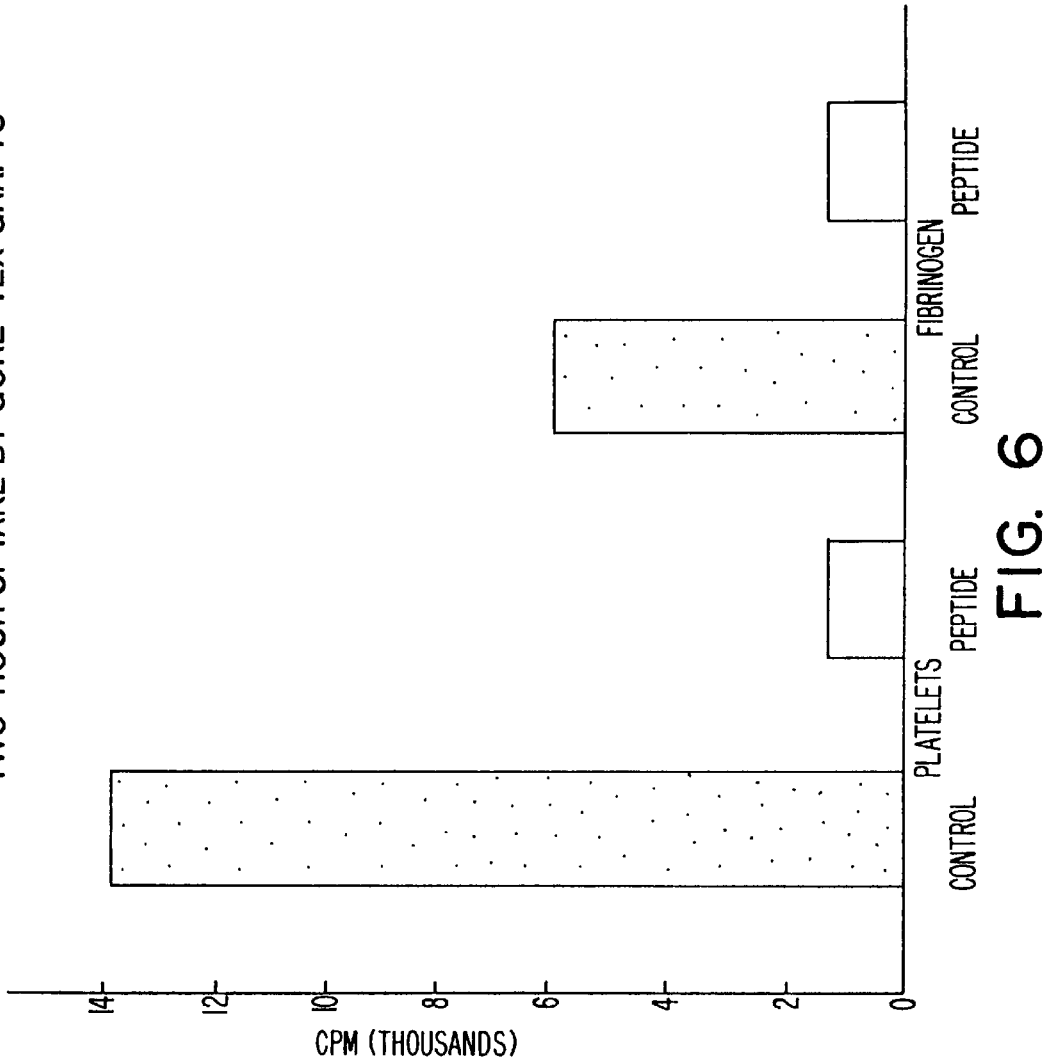

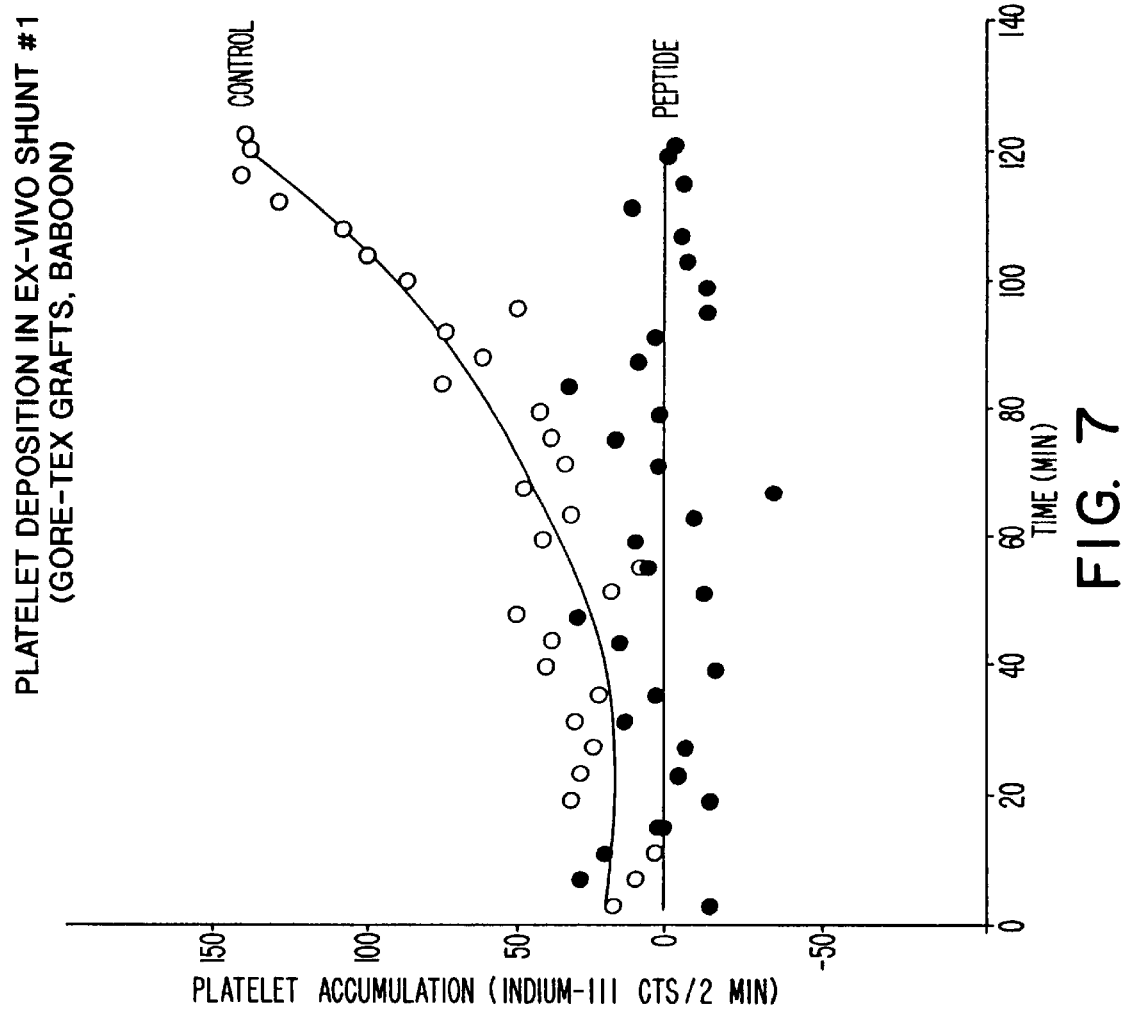

PEPTIDE EFFECTS ON ANIMAL HEMATOLOGY & BLEEDING TIMES
(Experiment 1)

| HEMATOLOGY PARAMETERS | SHUNT 1 | | SHUNT 2 | | |
|---|---|---|---|---|---|
| | 0 Hr. | 2 Hr. | 0 Hr. | 1 Hr. | 2 Hr. |
| Red Blood Cells (M/UL) | 4.78 | 4.00 | 4.49 | 4.70 | 4.11 |
| White Blood Cells (K/UL) | 9.3 | 4.0 | 12.0 | 11.4 | 8.8 |
| Platelets (K/UL) | 332 | 250 | 269 | 276 | 231 |
| Hematocrit (%) | 42 | 35 | 39 | 41 | 36 |
| Hemoglobin (G/UL) | 12.5 | 10.7 | 12.0 | 12.4 | 10.6 |
| Bleeding Time* (Min) | 4:48 | 4:55 | ND | 5:02 | 3:05 |
| Clotting Time (Sec) | 120 | 130 | ND | ND | 124 |

*Represents average of two simultaneous determinations.
ND-not determined.

FIG. 8

PEPTIDE EFFECTS ON ANIMAL
HEMATOLOGY & BLEEDING TIMES
(Experiment 2)

| HEMATOLOGY PARAMETERS | SHUNT 1 | | | SHUNT 2 | |
|---|---|---|---|---|---|
| | 0 Hr. | 2 Hr. | 0 Hr. | 1 Hr. | 2 Hr. |
| Red Blood Cells (M/UL) | 4.78 | 5.12 | 5.06 | 4.65 | 4.81 |
| White Blood Cells (K/UL) | 6.6 | 12.9 | 10.7 | 10.0 | 10.7 |
| Platelets (K/UL) | 274 | 281 | 281 | 264 | 286 |
| Hematocrit (%) | 39 | 41 | 41 | 37 | 38 |
| Hemoglobin (G/UL) | 12.3 | 13.2 | 12.9 | 12.0 | 12.4 |
| Bleeding Time* (Min) | 4:15 | 4:27 | ND | 4:46 | 4:05 |
| Clotting Time (Sec) | 131 | 125 | ND | ND | 132 |

*Represents average of two simultaneous determinations.
ND-not determined.

FIG. 11

METHOD AND COMPOSITION FOR TREATING THROMBOSIS

This application is a continuation of application Ser. No. 08/193,903, filed Feb. 9, 1994 now abandoned, which is a continuation of 08/032,449, filed Mar. 16, 1993, now abandoned, which is a continuation of 07/860,117, filed Mar. 30, 1992, now abandoned, which is a continuation of 07/506,444, filed Apr. 6, 1990, now abandoned.

BACKGROUND OF THE INVENTION

The invention relates generally to methods of treating thrombosis, and, more particularly, to such methods using peptides.

The formation of a blood clot within a blood vessel, termed thrombosis, is a serious condition, which can cause tissue damage and, if untreated, eventually death. Thrombotic formation is dependent upon platelet aggregation. The interaction of blood platelets with the endothelial surface of injured blood vessels and with other platelets is a major factor in the course of development.

Various products for dissolving such clots are now available, such as asprin, dipyridamole and heparin. These products generally kill or remove platelets which can eliminate the clot but has the potential serious side effect of causing prolonged bleeding. Moreover, the effect of such products can only be reversed by new platelets being formed or provided.

Platelet aggregation is dependent upon the binding of fibrinogen and other serum proteins to the glycoprotein GP IIb/IIIa complex on the platelet plasma membrane. GP IIb/IIIa is a member of a large family of cell adhesion receptors known as integrins, many of which are known to recognize an Arg-Gly-Asp (RGD) tripeptide recognition sequence. Individual receptor specificity is determined by the conformation that the RGD sequence adopts in each individual ligand. Inhibition of GP IIb/IIIa receptor binding, and therefore platelet aggregation, without inhibition of other cell adhesion receptors would be necessary for the prevention of coronary thrombosis.

There thus exists a need for a composition able to specifically inhibit the platelet aggregation receptor GP IIb/IIIa and to dissolve blood clots without removing or killing platelets and without causing detrimental side effects such as prolonged bleeding. The present invention satisfies this need and provides related advantages as well.

SUMMARY OF THE INVENTION

The invention provides RGD containing peptides which are cyclized and contain hydrophobic moieties adjacent to the carboxy terminus of the RGD sequence. Such peptides have an high affinity for the receptor IIb/IIIa and low affinity for the fibronectin and vitronectin receptors. Such peptides can be administered in a suitable physiologically acceptable carrier to therapeutically treat thrombosis in many forms.

BRIEF DESCRIPTION OF THE DRAWINGS

FIG. 4 shows the effects of the peptides injected in Example VII on coronary blood flow and thrombosis.

FIG. 5 shows the effects of the peptides injected in Example VII on hemodynamic responses.

FIG. 6 shows the platelet and fibrinogen uptake by Gore-Tex grafts in animal 1 injected with the peptide of Example VIII.

FIG. 7 shows the platelet uptake rates by Gore-Tex grafts in animal 1 injected with the peptide of Example VIII.

FIG. 8 shows the hematology parameters in animal 1 for control treatment (shunt 1) and for treatments with the peptide of Example VIII (shunt 2).

FIG. 11 shows the hematology parameters in animal 2 for control treatment (shunt 1) and for treatments with the peptide of Example VIII (shunt 2).

DETAILED DESCRIPTION OF THE INVENTION

Figure 1A:
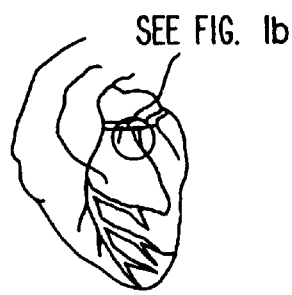
FIGS. 1A–1B diagram the insertion of electromagnetic flow probe, intra-coronary electrode and screw occluder into the left circumflex coronary artery (FIG. 1A) and shows coronary blood flow before and after adjustment of the critical stenosis (FIG. 1B).
Figure 1B:
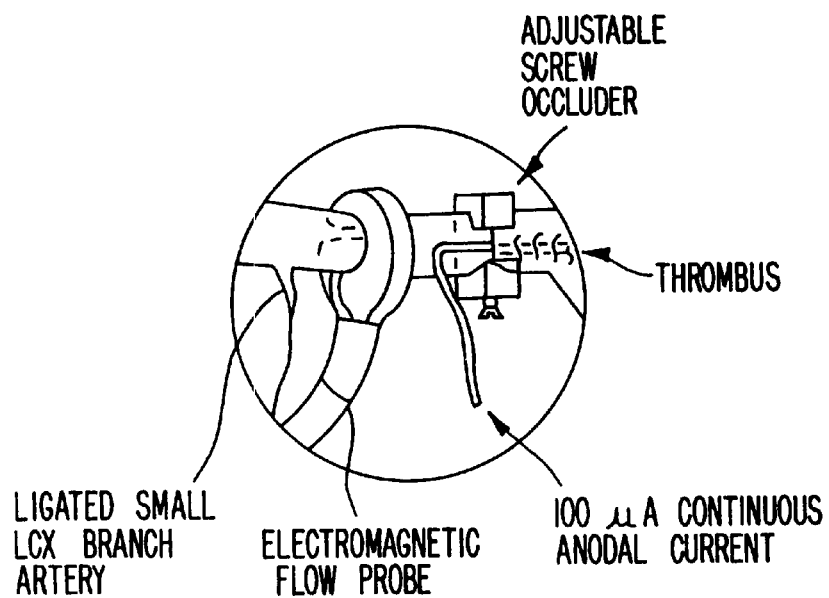
Figure 1C:
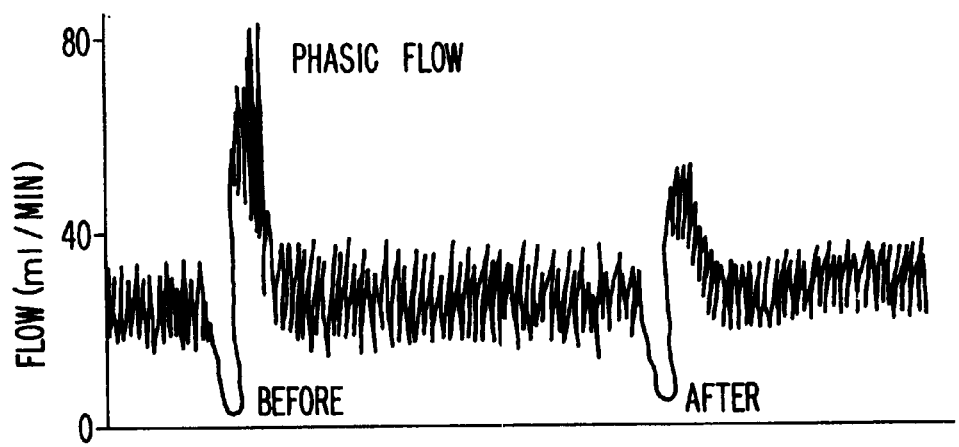
Figure 2A:
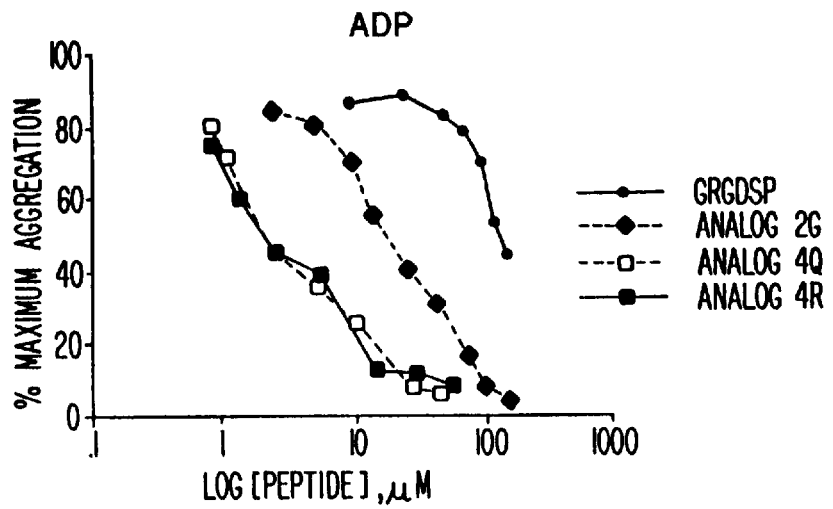
FIG. 2 is a dose-response analysis of the relative anti-aggregation potencies of the peptides injected in Example VII.
Figure 2B:
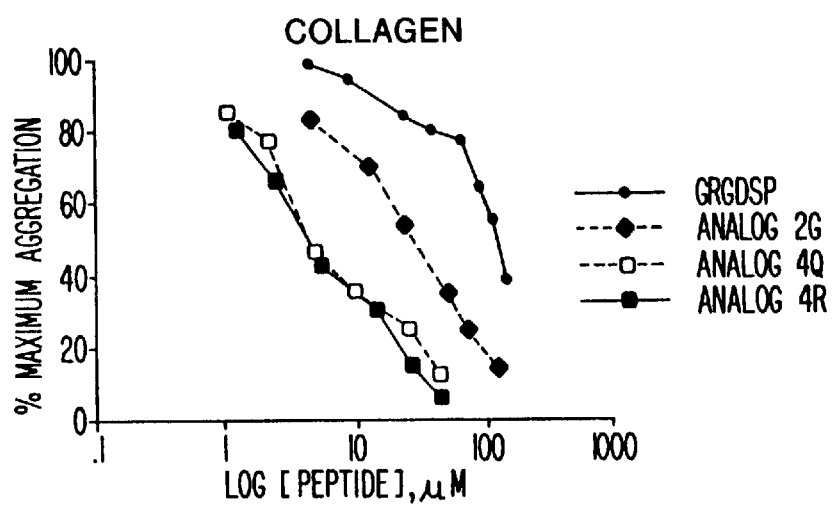
Figure 2C:
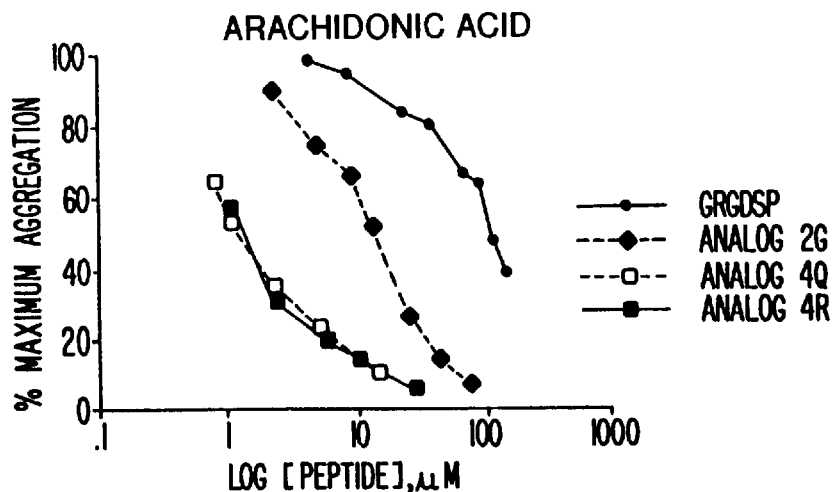

The invention provides novel peptides which are cyclic and contain the sequence RGDX wherein X is a hydrophobic moiety. These peptides are effective in inhibiting platelet aggregation and can therefore advantageously be used to dissolve blood clots as well as prevent inappropriate growth of vascular smooth muscle cells and arterial graft occlusion. Unexpectedly, such treatment does not cause the concomitant significant prolonged bleeding which has limited the usefulness of other anti-thrombotic agents. The use of such peptides is therefore a significant improvement over conventional therapy, including such therapy utilizing other RGD-containing peptides.

As used herein, references to "Arg-Gly-Asp containing peptides" or "RGD peptides" are intended to refer to peptides having one or more Arg-Gly-Asp containing sequences which may function as binding sites for a receptor of the "Arg-Gly-Asp family of receptors", i.e., those recognizing and binding to the Arg-Gly-Asp sequence. While the Arg-Gly-Asp sequence has been found to necessarily be invariant in order to retain the binding activity, the composition of the remaining peptide as well as any other chemical moiety present in conjunction with the peptide may vary without necessarily affecting the activity of the binding site. Where specific chemical structures or sequences beyond the Arg-Gly-Asp sequence are presented, it is intended that various modifications which do not destroy the function of the binding site are to be encompassed without departing from the definition of the peptide.

As used herein, the term "bridge" refers to a chemical bond between two amino acids, amino acid derivatives or other chemical moieties in a peptide other than the amide bond by which the backbone of the peptide is formed.

As used herein, the term "peptide bond" or "peptide linkage" refers to an amide linkage between a carboxyl group of one amino acid and the a-amino group of another amino acid.

As used herein, the term "peptide" is intended to include molecules containing amino acids linearly coupled through peptide bonds. Such peptides may additionally contain amino acid derivatives or non-amino acid moieties. The amino acids can be in the L or D form so long as the binding function of the peptide is maintained. Such peptides can be of variable length, preferably between about 4 and 200 amino acids, more preferably between about 9 and 35 amino acids most preferably, about 11 amino acids. The term amino acid refers both to the naturally occurring amino acids and their derivatives, such as TyrMe and PheCl, as well as other moieties characterized by the presence of both an available carboxyl group and amine group.

As used herein, the term "cyclic peptide" refers to a peptide having an intramolecular bond between two non-adjacent amino acids within a peptide. The intramolecular bond includes, but is not limited to; backbone to backbone, side-chain to backbone and side-chain to side-chain cyclizations. Various amino acid derivatives and chemical moieties are included in this group. Such structures include for example, Pen, Pmp and Pmp analogues and Pmc and Pmc analogues.

The one-letter and three-letter abbreviations for amino acids and other moieties used herein are given as follows:

| A | Ala | Alanine |
|---|---|---|
|   | α-ABA | α-Amino isobutyric acid |
| R | Arg | Arginine |
| N | Asn | Asparagine |
| D | Asp | Aspartic acid |
|   | Cha | Cyclohexyl-alanine |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
|   | napA | naphthyl-alanine analogues |
|   | Pas | 6,6-Cyclopentamethylene-2-Aminosuberic acid analogues |
|   | Pen | Penicillamine |
| F | Phe | Phenylalanine |
|   | PheCl | para-chloro-phenylanine |
|   | Pmp | $\beta_1,\beta$-Pentamethylene-$\beta$-Mercaptopropionic acid analogues |
| P | Pro | Proline |
| S | Ser | Serine |
|   | SuccAla | Succinyl-alanine |
| T | Thr | Theonine |
| W | Trp | Tryptophan |
| Y | Tyr | Tyrosine |
|   | TyrMe | para-methyl-Tyrosine |
| V | Val | Valine |

As used herein, the term hydrophobic is intended to include those amino acids, amino acid derivatives and chemical moieties which are non-polar. Hydrophobic amino acids include Phe, Val, Trp, Ile and Leu. Other hydrophobic moieties useful in the invention are TyrMe, PheCl and ChA.

It is now well-established that the amino acid sequence RGD is the cell binding site in a number of proteins, including for example, fibronectin, vitronectin and type IV collagen. The RGD binding site is recognized by a family of cell surface receptors, termed integrins. Platelets contain a large repertoire of RGD-cell surface receptors, each of which recognizes one or more RGD containing ligands to perform various physiological functions. GP IIb/IIIa is one such integrin receptor found in platelets. The ligands recognized by this receptor include fibrinogen and other serum proteins. GP IIb/IIIa is primarily responsible, through interaction with other platelets to form aggregates and through interactions with the endothelial surface of injured blood vessels, for the development of coronary artery thrombosis. When provided in soluble form, RGD peptides can inhibit cell attachment or platelet aggregation through competition with other RGD containing ligands. See for example U.S. Pat. Nos. 4,578,079, 4,517,686, 4,792,525 and 4,683,291, which are incorporated herein by reference.

Peptides containing RGD sequences can be synthesized by means well known in the art. Preferably, they are synthesized using an automated peptide synthesizer, such as those manufactured by Applied Biosystems, Inc., Foster City, Calif. Cyclization can be achieved where the peptides contain two sulphur-containing amino acids, or other moieties through a disulfide bond. Examples of useful sulphur-containing moieties are Cys and Pen and Pmp. Alternatively, cyclization can be accomplished through the formation of a peptide bond or alkyl bridge structures using for example Pas.

Such peptides may be synthesized by any suitable method, including well-known methods of chemical synthesis. Preferably, the linear sequence is synthesized using commercially available automated peptide synthesizers. The material so synthesized can be precipitated and further purified, for example by high performance liquid chromatography (HPLC). Although a purity of greater than 95 percent for the synthesized peptide is preferred, lower purity may be acceptable.

To obtain one of the hydrophobically enhanced peptides of the present invention which have a high potency for inhibiting platelet aggregation and low affinity for other RGD cell surface receptors, the synthesized peptide is cyclized using methods well known in the art. For example, where the residues contain sulfhydryls, a disulfide bridge may be formed by oxidizing a dilute aqueous solution of the peptides with $K_3[F_e(CN_6)]$. Other residues, such as the chemical moieties Pmp and Pas can create a bridging structure through a disulfide bond between Pmp and Cys (or similar structures) and an alkvl bond between Pas and an amino acid methylene moiety (or similar structures). Other means of cyclizing, which are known in the art, may also be utilized.

The cyclized peptides of the present invention can also be prepared by forming a peptide bond between non-adjacent amino acid residues. A procedure for forming such peptide bond is provided in Schiller et al., Int. J. Peptide Protein Res. 25:171 (1985), which is incorporated herein by reference. Briefly, cyclic peptides can be synthesized on the Merrifield resin by assembling the peptide chain using $N^\alpha$-Fmoc-amino acids and Boc and Tertiary-butyl protein.

Side-chain to side-chain cyclizations can be performed by the above procedure or using $N^\alpha$-Boc-amino acids together with OFm/Fmoc side-chain protection for Asp and Lys residues as described by Felix et al, Int. J. Peptide Progein Res. 31:231 (1988), which is incorporated herein by reference. Alternatively, side-chain to backbone cyclizations can be performed using this procedure or in combination with the procedure described in the preceeding paragraph.

The peptides of the present invention contain a hydrophobic moiety adjacent the carboxy terminus of the RGD sequence. Appropriate hydrophobic moieties include for example Phe, Trp, Val, Ile, Leu, PheCl, TryMe, and ChA. Such peptides can be represented as $X_2X_3X_4RGDX_1X_5X_6$ wherein $X_1$ is a hydrophobic moiety; $X_3$ and $X_5$ are moieties capable of forming a bridge, such as a disulfide bridge, alkyl bridge or a peptide bond. Representative of these moieties are Cys, Pen, Pmp and Pas. $X_2$ and $X_6$ are 0 to 50 amino acids. When the number of residues of $X_2$ is one, X2 is preferably a Gly; when the number of residues is greater than one, the carboxy terminal residue is preferably a Gly. $X_4$ is 1 to 10 amino acids, preferably with His as the carboxy terminal residue. Specific peptides of this nature include RP enGRGDWPCR, GPenGHRGDLRCA, RP enGHRGDWRCR, RPenGHRGD(ChA)RCR, P mpGHRGDLRCA, G(dPen)GHRGDLRCA, R(am-P mp)GHRGDWRCR, R(am-Pmp)GHRGD(TyrMe)RCR, R(am-Pmp)GHRGD(PheCl)RCR, R(am-P mp)GHRGDLRCR, R(am-Pmp)GHRGDLRCR, R(t-but-am-Pmp)GHRGDLRCR.

In another aspect of the invention, peptides are selected that posses high affinity for IIb/IIIa and low affinity for the fibronectin and vitronectin receptors. Such IIb/IIIa affinity can be determined, as for example, by a liposome attachment assay, as described in Examples IV and VI or in a platelet aggregation assay as described in Example V. Peptides characterized by high affinity for IIb/IIIa will have an $IC_{50}$ as measured under the assay conditions provided in Examples IV and VI of less than about 10 μm, preferably less than about 1 μm, more preferably about 0.1 μm. Alternatively, affinity for IIb/IIIa as characterized in Example V will have an $IC_{50}$ of less than about 10 μm, preferably less than about 1 μm, more preferably about 0.1 μm. Fibronectin receptor affinity and vitronectin receptor affinity can be determined as for example by the methods detailed in Examples III and VI, and IV and VI respectively. Using these assays, under the conditions described, peptides having low affinity for the fibronectin receptor will have an $IC_{50}$ of greater than about 0.1 μm, preferably greater than about 1 μm, more preferably greater than about 10 μm; low affinity for the vitronectin receptor is greater than about 1 μm, preferably greater than about 10 μm, more preferably greater than about 100 μm. It is thus possible to screen various peptides in order to determine their inhibitory concentrations, and therefore binding affinities, and to select those having high affinity for the vitronectin receptor and low affinity for the fibronectin and vitronectin receptors.

The peptides of the present invention can be utilized to effectively eliminate thrombotic conditions by administering to a mammal exhibiting thrombosis a therapeutically effective amount of the peptide in a suitable physiologically acceptable carrier. Effective amounts will be 1 to 50 mg/kg/hr body weight, preferably about 5 to 10 mg/kg body weight. Appropriate effective amounts can be easily determined by those skilled in the art. The peptide can be administered in a variety of ways, as for example, by infusion or injection. Length of treatment can be determined by monitoring effect.

The following Examples are intended to illustrate but not limit the invention.

EXAMPLE I

Peptide Synthesis

Peptides were synthesized on an automated peptide synthesizer (Model 430A, Applied Biosystems, Foster City, Calif. USA) using optimized n-methyl pyrrolidone chemistry on PAM resin as recommended by the manufacturer. Cleavage of the peptides from the resin was achieved with 100% hydrogen fluoride. The peptides were further purified by HPLC using a VYDAC reverse phase $C_{18}$ column with 0 to 60% acetonitrile gradients. Peptides were used only if found to be ≧98% pure.

For Pen cyclization, 611 mg of the peptide synthesized as described above were dissolved in 4 liters of water that had been previously boiled and allowed to cool. Immediately prior to addition of the peptide, nitrogen was bubbled through the water for 45 minutes. After the peptide was dissolved, a solution of 0.1 μg/ml of potassium ferrous cyanide $K_3[Fe(CN)_6]$ in water was added dropwise to the stirred peptide solution until the yellow color persisted for 5 minutes (approximately 5 ml). The pH of the solution was held at 7.0 throughout this procedure by addition of $NH_4OH$. The solution was allowed to stand for 20 hours under low vacuum and then lyophilized. Excess $K_3[Fe(CN)_6]$ was removed by passing the cyclized material over a Sephadex G-15 column (1.8×120 cm). The peptide was purified by reverse phase HPLC using a Waters Bondapak™ $C_{18}$ column (3×30 cm; 10 μm packing) (Waters Assoc., Milford, Mass.). The peptide was loaded on the column in buffer A (20 mM ammonium acetate at pH 7.5) and eluted with a gradient of buffer B consisting of 60% acetonitrile and 40% buffer A. Eluted fractions were tested for their ability to inhibit receptor binding.

The major peak obtained from the $C_{18}$ column constituted 90% of recovered peptide and was deduced to be a monomeric cyclic peptidet because it was retained on the column for the length of time predicted for that sequence and because the uncyclized material and multimeric forms were well separated from the main peak.

EXAMPLE II

Receptor Purification

Receptors were purified according to the procedures of Pytela et al. (Methods Enzymol. 144:475 (1987)), incorporated herein by reference. Briefly, vitronectin receptor (Vn-R) was purified by RGD peptide-affinity chromatography from (100 mM) octyl glucoside (OG) extracted human placenta. After extraction, the suspension was filtered over a Sepharose 6B column and then applied to a GRGDSPK column. Except where stated, all procedures were carried out at 4° C. The peptide column was washed with three volumes of Tris-buffered saline (TBS) containing 1 mM $Ca^{2+}$ and 25 mM OG and then with TBS containing 1 mM $Ca^{2+}$ and 25 mM octyl thioglucoside (OTG) at room temperature. Elution of bound receptor was achieved at room temperature with TBS containing 20 MM EDTA and 25 mM OTG. Finally, $Ca^{2+}$ and $Mg^{+2}$ were added to eluted fractions to achieve final concentrations of 1 mM for both ions.

Fibronectin receptor (Fn-R) was similarly purified from (100 mM) octyl glucoside-extracted human placenta using a procedure identical to that for the Vn-R up to and including the initial Sepharose chromatography step. The Sepharose 6B column flow-through was brought to 2 nM $Mn^{+2}$ and the resulting solution was run over a 110 kd fibronectin fragment-affinity column. Washing and elution steps were identical to those used in purifying vitronectin receptor.

The purity of each receptor was assessed with SDS-PAGE under reducing and non-reducing conditions. Each receptor was flash-frozen in liquid nitrogen and stored frozen until use.

EXAMPLE III

Enzyme-Linked Immunosorbent Assay (ELISA) for Fibronectin Receptor (FN-R)

Peptide binding to purified Fn-R was determined by using a competitive enzyme-linked immunosorbent assay (ELISA) in which fibronectin is immobilized and the binding of solubilized Fn-R is detected with labeled anti-FnR antibodies in the presence of various concentrations of peptide analogue.

Microtiter plates were coated with 110 μl of human fibronectin (at 2 μg/ml) in TBS. The plates were washed three times with TBS that contained 0.05% Tween 20. If necessary, peptides were added after this washing in 10 microliter aliquots. The fibronectin receptor was then added in 2-fold serial dilutions with TBS containing 20 mM octyl glucoside and 2 mM MnCl$_2$. The plates were incubated for three hours at room temperature, washed with 200 μl of the above TBS-Tween buffer. 100 μl of affinity-purified rabbit anti-human fibronectin receptor antibody was added to the wells and the plates were incubated for an additional two hours, washed twice with TBS-Tween and then distilled water. Affinity-purified goat anti-rabbit IgG conjugated to horseradish peroxidase (100 μl) was then added to each well. Bonding reactions were incubated for 16 hours at room temperature. The following day, the plates were washed twice with TBS-Tween and then distilled water. 100 μl of substrate mixture (10 mg O-phenylenediamine in 25 ml 0.1 M citrate-phosphate buffer, pH 5.0, plus six microliters of 30% H$_2$O$_2$) was added to the plates and allowed to develop. The development process was stopped by adding 50 μl of 4N H$_2$SO$_4$ to each well.

EXAMPLE IV

Liposome Attachment Assay for Vitronectin Receptor (Vn-R)

This assay was performed with minor modifications, according to the method of Pytela et al., Methods Enzymol. 144:475 (1987), incorporated herein by reference. Briefly, 1:4 mixture of labelled and unlabelled phosphatidylcholine (PC) liposomes was dissolved under nitrogen and diluted with an equal volume of purified receptor (purified as described in Example II) to achieve a fixed predetermined receptor-liposome concentration ratio. This mixture was then dialyzed overnight at 4° C. in phosphate buffered saline (PBS) containing 1 mM Ca$^{2+}$. An aliquot of the dialyzed sample was counted to assess radioactive content; the receptor-liposome mixture was then diluted to obtain a set radioactivity per unit volume.

Microtiter plates were coated with 10 μg of vitronectin. Non-specific sites were blocked for 2 hours at 37° C. in PBS containing 5 mg/ml BSA and 1 mM each of CaCl$_2$ and MgCl$_2$. The plates were then rinsed twice with PBS containing 1 mM Ca$^{+2}$ and Mg$^{+2}$, and 100 μl of the liposome-receptor mixture was added to each well. If necessary, peptides were added before this step in a 1–10% dilution. The plates were then incubated at 4° C. for 24 hours. The following day, the liquid in each well was aspirated and the plates were washed twice with PBS containing 1 mM Ca$^{+2}$ and Mg$^{+2}$. Finally, 100 μl of 2% SDS was added, the plates were shaken for 10–15 minutes, and the supernatants were collected, vortexed, and subjected to liquid scintillation counting. This procedure typically yielded ca. 1000 total and 100 non-specific counts per well.

EXAMPLE V

Platelet Aggregation and Potencies of Hydrophobically Enhanced RGD Peptides

Platelet aggregation was assessed using the method of Born, Nature 194:927–929 (1962), incorporated herein by reference. Briefly, the change in light transmission was measured through a stirred suspension of platelets in an aggregometer (Model 400 VS, Chrono-Log, Havertown, Pa., USA). Studies employing ADP were performed with platelet-rich plasma (PRP), which was obtained by low-speed centrifugation (200×g for 10 min.) of whole blood freshly drawn into trisodium citrate (at a final concentration of 11 mM). In studies using thrombin, the PRP was gel-filtered on Sepharose 2B in divalent ion-free Tyrode's solution containing 2% BSA. For all studies, the reference standard was platelet-poor plasma, which was obtained by centrifuging PRP at 1000×g for 5 min.

All aggregation studies were performed at 37° C. with a constantly stirred suspension of 3×10$^8$ platelets/ml. (Platelet count was determined with the aid of a hemacytometer.) Peptides and stimulants were added to these suspensions in 1% dilutions. The PRP and gel-filtered platelets were used within three hours from the time of blood collection.

Peptide anti-aggregation potencies were determined from dose-responsive curves for the inhibition of the maximum aggregation responses stimulated by physiologic doses of ADP (10 μm) and thrombin (2 U/ml). The 50% inhibitory concentration of each peptide (IC$_{50}$) was determined by regression analysis of these curves.

The hydrophobically enhanced RGD peptides have been grouped into three distinguishable classes for systematic comparison. They are (1) cyclic RGD peptides which vary the size and hydrophobicity of the moiety at the position immediately following the Asp residue in the tripeptide RGD (the first and last position as depicted in Table I may vary by substitution with Arg); (2) cyclic RGD peptides which vary the size and hydrophobicity of the bridging structure for cyclization and (3) cyclic RGD peptides which vary the size and hydrophobicity of both the bridging structure and the residue immediately following the Asp residue in the tripeptide RGD. Other RGD peptides, both linear and cyclized, are included in Table I for comparison. Underlining indicates a bridge between the first and last residue included in the underlined portion.

As shown in Table I, each class of cyclized, hydrophobically enhanced RGD peptide analogue demonstrated inhibitory effects on platelets stimulated with thrombin or ADP. Eight analogues had inhibitory potencies (IC$_{50}$) less than or approximately equal to 10 μm against thrombin-stimulated platelet aggregation while as many as twenty-two demonstrated inhibitory potencies in this range for the ADP-stimulated response. For example, the inclusion of hydrophobic residues phenylalanine (F) and tryptophan (W) in the "X" position of template structures GP enGRGD-X-PCA and GPenGHRGD-X-RCA imparted greater anti-aggregation inhibitory potency relative to GP enGRGDSPCA and GPenGHRGDLRCA. This effect was further enhanced by other non-natural hydrophobic structures, such as para-chloro-phenylalanine (PheCl) and para-methyl-tyrosine (TryMe), in the same position. However, and not wishing to be bound by this statement, larger hydrophobic structures, such as 1-naphthyl-alanine and 2-naphthyl-alanine were ineffective, indicating that size must be limited to obtain maximum efficacy. The inclusion of arginine (R) or lysine (L) in the "X" positions of XP en-GRGDSPCA or X-PenGHRGDLRCA also increased anti-aggregation potency. Organic mimic bridging structures were substituted for penicillamine and Pmp in the "X" position of the template structure G-X-GHRGDLRCA. When substituted alone, tert-butyl-Pmp and amino-Pmp lessened peptide anti-aggregation potency. On the other hand, peptide derivatives containing these moieties and an N-terminal R significantly out-performed the previously disclosed cyclic RGD structures GPenGHRGDLRCA and P mpGHRGDLRCA, in platelet aggregation assays. Finally, replacement of 1-Pen in G (1-Pen)GHRGDLRCA by the d-form of penicillamine lowered anti-aggregation potency by 2-fold.

The modifications described above have resulted in inhibitory potencies 10 to 250-fold more potent than the prototype GRGDSP linear peptide and 2 to 50-fold more potent than the initial conformationally restrained cyclic peptide GPenGRGDSPCA.

TABLE I

Potencies of Hydrophobically Enhanced RGD Peptide Analogs Against Platelet Aggregation and Receptor Binding

| Peptide | Thrombin Stimulated Aggregation | ADP-Stimulated Aggregation | FnR Binding | VnR Binding | IIb/IIIa Binding |
| --- | --- | --- | --- | --- | --- |
| GRGDSP | | 135 ± 15 | 0.032 ± 0.006(4)* | 0.70 | 50 |
| GPGRGDSPCA | | 27.5 | 0.015 | 0.15 | 20 |
| GPenGRGDTPCA | 28 | 22.3 | .063 | 0.47 | |
| GPenGRGDLPCA | | 19.3 | | 4.2 | |
| GPenGRGDFPCA | | 3.5 | .084 | 2.7 | |
| GPenGRGDWPCA | | 1.6 | 0.13 | 12.7 | |
| RPenGRGDSPCR | | | | | |
| RPenGRGDWPCR | 0.53 | 0.65 | 0.014 | 4.2 | 0.43 |
| GPenGHRGDLRCA | 18 | 15 | | 1.2 | 10 |
| RPenGHRGDLRCR | 3.2 | 10.3 | 5.9 | 37.1 | 6.2 |
| RPenGHRGDWRCR | 1.2 | 1.3 | 7.3 | 0.71 | 0.80 |
| RPenGHRGD(ChA)RCR | | 4.1 | 3.9 | | |
| RPenGHRGD(1-napA)RCR | | 29 | | | |
| PmpGHRGDLRCA | 6.3 | 7.2 | 0.34 | 0.41 | |
| G(am-Pmp)GHRGDLRCA | | 83 ± 23(2) | 3.4 | | |
| (t-but-am-Pmp)GHRGDLRCA | | 120 | 1.1 | | |
| (t-but-am-Pam-Pmp)GHRGDLRPenA | | 89 | | | |
| G(dPen)GHRGDLRCA | | 6.28 ± 0.7(2) | | | |
| R(am-Pmp)GHRGDWRCR-1 | | 1.4 | 1.7 | | |
| R(am-Pmp)GHRGDWRCR-2[a] | | 1.4 | 1.7 | | |
| R(am-Pmp)GHRGD(TyrMe)RCR | | 0.45 | 2.1 | | 0.35 |
| R(am-Pmp)GHRGD(PheCl)RCR | | 0.65 | 1.2 | | |
| R(am-Pmp)RGD(ChA)CR | | <200* | | | |
| R(am-Pmp)GHRGDLRCR-1 | 1.3 | 1.5 | | | |
| R(am-Pmp)GHRGDLRCR-2[a] | 1.3 | 1.5 | | | |
| R(t-but-am-Pmp)GHRGDLRCR-1 | | 1.9 | 2.2 | | |
| R(t-but-am-Pmp)GHRGDLRCR-2[a] | | 1.9 | 2.2 | | |
| R(am-Pmp)GRGDWPCR | | 1.2 | | | |
| GRGDSPDG | | 32 | 0.005 | 0.10 | |
| FRGDSPDG | | 110 | 0.12 | | |
| YRGDSPDG | | 83 | 1.1 | | |
| LRGDSPDG | | 150 | | | |
| dSRGDSPDG | | 54 | .075 | 0.07 | |
| VRGDSPDG | | 92 | 0.04 | | |
| GPenGRGDRPCA | | 22.3 | .063 | 0.47 | |
| GPenLRGDTPCA | | 86 | | | |
| GPenVRGDSPCA | | 45 | | | |
| GPenYRGDSPCA | | 47 | | | |
| GPenLRGDSPCA | 308 | 415 | | | |
| GPenLRGDSRCA | 49 | 41 | | 1.35 | |
| GPenGRGDSFCA | | 115 | | 0.02 | |
| GPenFRGDSFCA | | >200 | | | |
| GPenGRGDTPCR | | 22.0 | | | |
| RPenGRGDTPCA | 3.1 | 7.0 | | 5.6 | |
| KPenGRGDTPCA | | 10.3 | | | |
| RPenGRGDTPCR | 2.0 | 6.3 | .027 | 2.56 | |
| RPenGRGDTPCK | | 7.6 | | | |
| RPenGRGDSRCA | 12 | 12 | | | |
| RPenGRGDLRCA | 13 | 16 | | | |
| GPenGHRGDTRCA | 17 | 11.3 | 2.9 | | |
| R₂PenGRGDTPCA | 2.7 | 8.2 | | | |
| RPenGHRGDTRCR | | 8.8 | | | |
| LPenGHRGDLRCA | | 10.5 | | | |
| PmoGRGDSPCA | | 45 | .023 | | |
| PmpGRGDTPCA | | 85 | .086 | 0.50 | |
| PmpGHRGDLRPRnA | | 5.8 | .078 | >50 | |
| (t-butylAmino-Pmp)GHRGDLRCA | | 130 | | | |
| R(AminoPmp)GRGDTPCA | | 54 | | | |
| GHRGDLRDASG | | 7.5 | 4.9 | 36.8 | |
| RKGHRGDLRDLR | | 75 | 1.3 | | |
| R(orn)GHRGDLRDRASG | | 24 | | | |
| R(orn)GHRGDLRDR | | >200 | | | |
| R(orn)GHRGDLRER | | 44 | 1.7 | | |
| GHRGDLRPasA-NH₂ | | 28 | 0.64 | | |
| R₉GDS | | 28 | 0.64 | | |

*concentrations unconfirmed by amino acid composition analysis
[a]Represents second peak after HPLC purification of synthesized peptides using a racemic am-Pmp mixture.

EXAMPLE VI

Peptide Receptor Selectivity

In parallel studies with the platelet aggregation experiments (described in Example V), the apparent affinities of peptides for GP IIb/IIIa, fibronectin and vitronectin receptors were determined. Receptor-binding assays (as described in Examples III and IV) with purified receptors, were used to assess the abilities of the peptides to displace the binding of receptors to their receptor-specific ligands.

Shown in Table I, as a comparison with platelet inhibitory potencies, are the relative affinities of each peptide for the receptors shown.

The binding data are again represented as the 50% inhibitory concentration of each peptide ($IC_{50}$s) and were determined as described in Example V for the dose-response curves for the inhibition of platelet aggregation. $IC_{50}$s for FnR were determined by ELISA (Example III). Those for VnR and GP IIb/IIIa were determined by liposome attachment assay (Example IV). The GRGDSP prototype peptide is used as a reference for comparison between assays for an individual peptide.

EXAMPLE VII

Efficacy Against Electrically Induced Canine Coronary Thrombosis

Surgical Preparation and Instrumentation

Male mongrel dogs weighing 14 to 20 kg were selected based on proper aggregation of their platelets in response to arachidonic acid, collagen, and adenosine disphosphate (ADP) and based on similar weights and hemodynamic properties.

Before surgery, the animals were anesthetized with sodium pentobarbital (30 mg/kg, i.v.) and then intubated and ventilated on room air with positive pressure using a respirator (Harvard Apparatus, S. Natick, Mass.) at a volume of 30 ml/kg and a frequency of 12 breaths/min. Surgery, performed under aseptic conditions, was begun with the placement of cannulae into the left carotid artery and jugular vein for monitoring arterial blood pressure (Statham P23 pressure transducer, Gould, Inc., Cardiovascular Products, Oxnard, Calif.) and administering intravenous fluids.

Figure 3A:
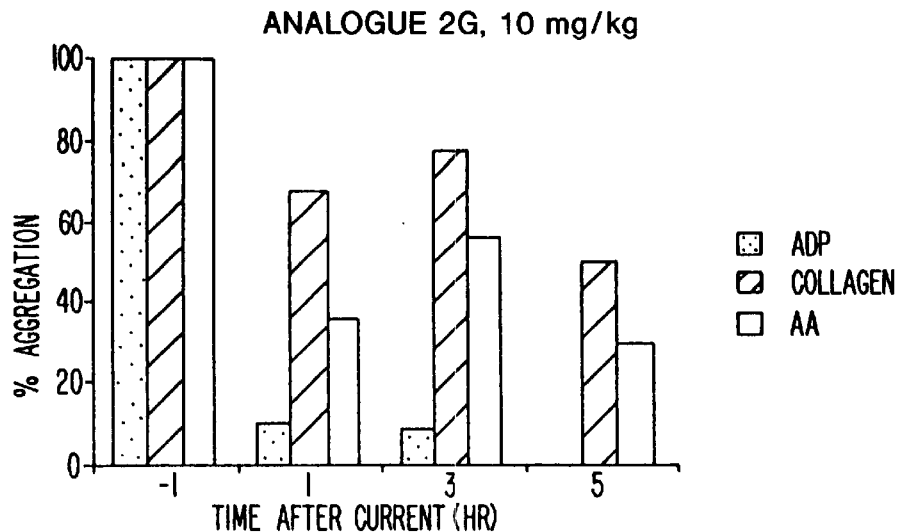
FIGS. 3A–3B shows the platelet aggregation values for each peptide dose following time after induction of coronary thrombosis.
Figures 1, 3B:
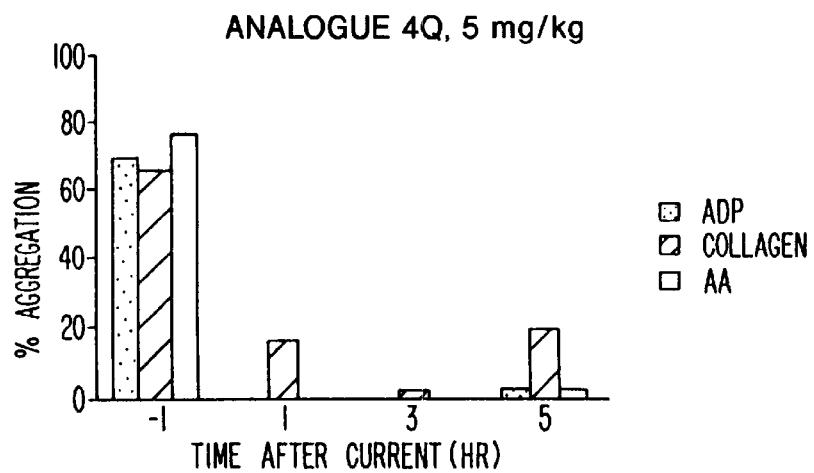

The heart was exposed via a left thoracotomy through the 5th intercostal space. A 2-cm segment of the left circumflex coronary artery (LCCA) was isolated from surrounding tissue by blunt dissection. This artery was instrumented from proximal to distal with an electromagnetic flow probe (Model 501, Carolina Medical Electronics, Inc., King, N.C.), intra-coronary electrode, and screw occluder (see FIG. 1). The intra-coronary electrode was constructed by attaching a 25-gauge hypodermic needle tip to a 30-gauge Teflon-insulated silver-coated copper wire. The mechanical occluder was constructed of stainless steel in a C shape with a Teflon screw (2 mm diameter) on top. It was adjusted to control vessel circumference and decrease the reactive hyperemic flow due to a 10-sec (full) occlusion by 50–70% without affecting basal coronary blood flow (FIG. 1). A monopolar epicardial electrode was sutured to the surface of the ventricle in the region of LCCA distribution to monitor ischemic changes in the electrocardiogram (ECG). The left atrium was cannulated with polyethylene tubing for administration of the peptide. Continuous recordings of blood pressure, limb lead II ECG, epicardial electrogram, and mean and phasic LCCA blood flow were obtained on a Model 7 polygraph (Grass Instrument Co., Quincy, Mass.). Induction of Coronary Thrombosis One hour after the completion of surgery, a 100 microamp continuous anodal direct current delivered from a 9 volt nickel-cadmium battery was applied to the intimal surface of the LCCA. The anode of the battery was in series with a 250,000 ohm potentiometer and the intraluminal coronary artery electrode. The electric circuit was completed by placing the cathode in a subcutaneous site. Electrical stimulation was applied for three hours. At the conclusion of each experiment, the heart was fibrillated electrically and quickly removed, and the LCCA was dissected free as far as possible to verify the position of the implanted anodal electrode.

For all ex vivo studies (see FIG. 3), control aggregation values were standardized to the percentages of light transmission observed in PRP and PPP samples (0% and 100%, respectively).

Peptide Administration

Animals were randomly assigned to two treatment groups: vehicle control (i.e., normal saline) or RGD peptides at various concentrations. Peptides were administered intraatrially in both bolus and continuous injections. Each bolus injection consisted of 5 or 10 mg/kg and was administered 15 minutes before application of the current. A continuous infusion of the same peptide was then started immediately after completion of this initial injection. Animals that received a 5 mg/kg bolus also received a 5 mg/kg/hr infusion, whereas animals that received a 10 mg/kg bolus also received a 10 mg/kg/hr infusion. The anti-thrombotic effects of the peptides were monitored until 30 minutes after the occurrence of a persistent, occlusive thrombus or five hours after the initiation of electrical stimulation (whichever resulted first). If an occlusive thrombus had not developed within four hours after the initiation of current, the peptide infusion was stopped.

Platelet Studies

Platelet counts and ex vivo aggregation studies were performed one hour before and 1, 3, and 5 hours after application of anodal direct current. Samples of arterial blood were drawn into plastic syringes containing 3.8% trisodium citrate (giving a 1:10 final dilution) and platelet aggregation determined as described in Example V.

Figures 2, 3B:
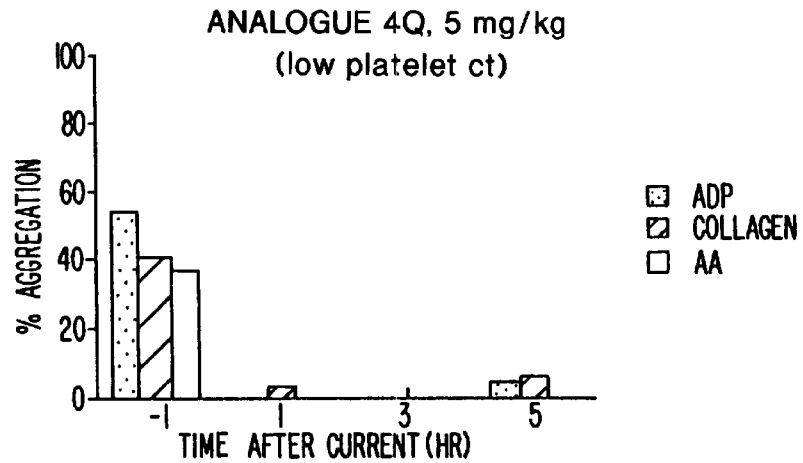

The inhibitory potencies of peptide analogues 2 G (GP enGHRGDLRCA), 4Q (RPenGHRGDWRCR), and 4R (RP enGRGDWPCR), as well as the generic analogue GRGDSP, were determined against canine platelet aggregation stimulated maximally by 10 μm ADP, 0.65 mM arachidonic acid (AA), or 9.6 micrograms/ml collagen. Epinephrine (550 nM) was used to prime platelets before stimulation with arachidonic acid. Peptides were added in 1% dilutions to the PRP solutions. The relative anti-aggregation potencies of all injected peptides and the generic analog GRGDSP were determined at the 1 hour before current time point, with dose-response analysis (see FIG. 2). The peptide concentrations causing 50% inhibition of maximal activation ($IC_{50}$s) were derived by linear regression of these dose-response curves. For computation of these inhibitory potencies, control values (i.e., in the absence of peptide) were considered as 100% of maximum.

As shown, analogues 4Q and 4R exhibited superior potencies, inhibiting aggregation by 50% at 1.5–5 μm. Analogue 2G was slightly less potent, with $IC_{50}$s of 15–30 μm, whereas GRGDSP inhibited all three responses by 50% at ca. 130 micromolar. Notably, the potency order (4Q=4R>2G>GRGDSP) and $IC_{50}$s of these peptides against these responses were the same as those observed for their inhibition of ADP-, collagen-, and arachidonic acid-stimulated aggregation of human platelets.

Platelet aggregation was also determined ex vivo at one, three, and five hours after current application. For these studies, arachidonic acid, or collagen was again used to stimulate the platelets.

Figures 3, 3B:
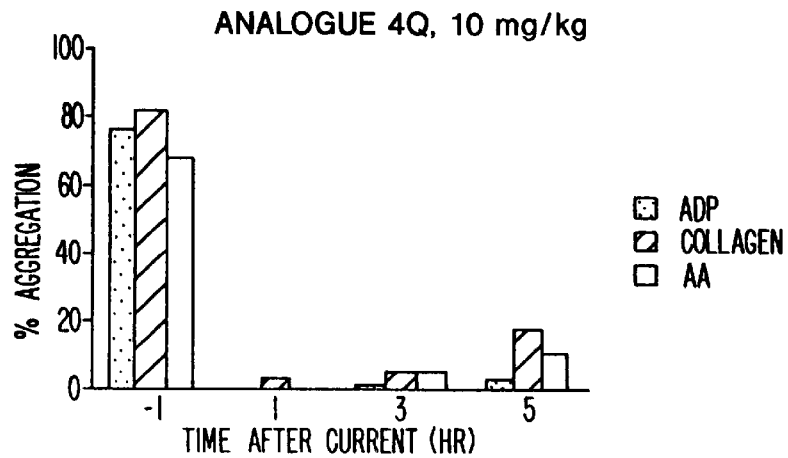
Figures 1, 3C:
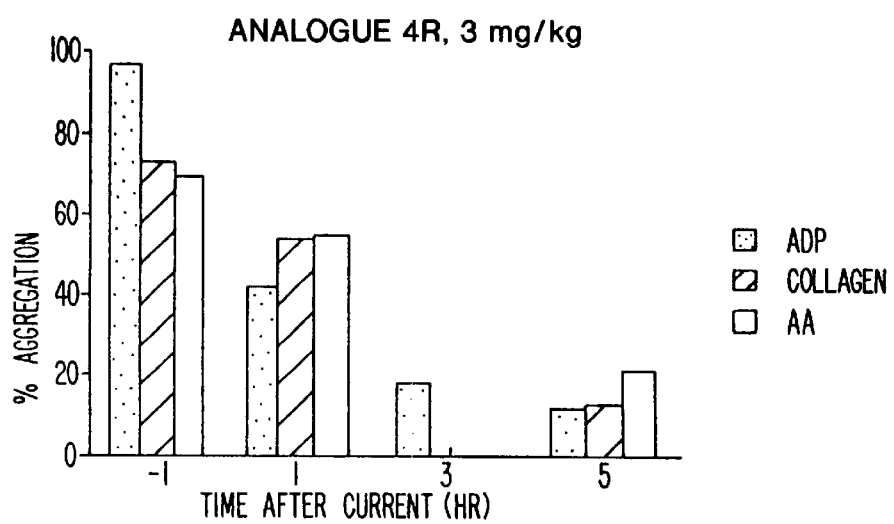
Figures 2, 3C:
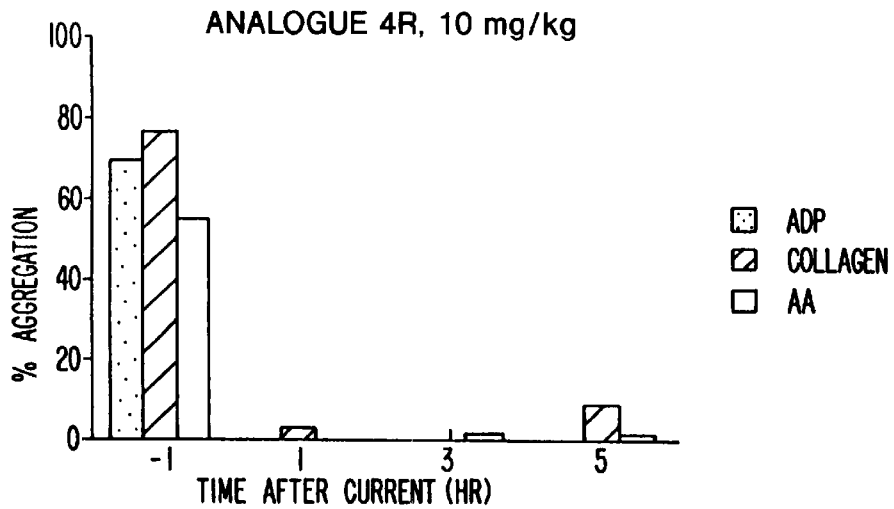

The average aggregation values determined in these studies for all of the peptide treatments are depicted in FIG. 3. (In these histograms, 0% and 100% aggregation represent the extent of light transmission through PRP and PPP, respectively, before the addition of stimulant.) Analogue 2G, when injected at 10 mg/kg, substantially inhibited ADP-stimulated aggregation but only partially inhibited the AA- and collagen-stimulated responses (43–70% and 12–50%, respectively, relative to control levels) at all three time points (FIG. 3a). As shown in FIG. 3b and 3c, the ex vivo anti-aggregation effects of analogues 4Q and 4R were far superior. A 5 mg/kg injection of analogue 4Q made the platelets completely unresponsive to stimulation with ADP and AA at all three time points and caused near-maximal inhibition of their activation by collagen. (Here, the absence of a coded bar indicates the absence of the corresponding response.) As shown in FIG. 3b, the effects of this same peptide at the same injection were more pronounced when platelet count was low, i.e., ca. one-third of normal (104, 000/ml vs. 361,000/ml). At a higher injected concentration (10 mg/kg), analogue 4Q prevented platelet aggregation by all three stimuli at one-and three-hour time points. At the five-hour point, platelet responsiveness was slightly improved. The control responses in these studies were 70–80% of maximum. As shown in FIG. 3c, analogue 4R, at 3 mg/kg, exerted an apparent time-dependent effect on platelet responsiveness in that aggregation was reduced only 20–58% at one hour but 75–100% at three and five hours relative to control levels. Finally, a 10 mg/kg injection of this analogue caused the platelets to be unresponsive to all modes of stimulation at all time points. Here the control responses were 55–80% of maximum.

Peptide Effects on Coronary Blood Flow and Thrombosis

Coronary thrombosis was quantified as the time to full occlusion. The effects of the various peptide treatments on coronary thrombosis is illustrated in FIG. 4. In the control situation (saline injections), a full occlusion was observed in slightly more than two hours. Analogue 2G, even at 10 mg/kg, did not significantly influence this frequency. Analogue 4Q at 5 mg/kg significantly prolonged the time to occlusion and at 10 mg/kg completely prevented occlusion for the full five-hour experimental period. Moreover, at the low dose (5 mg/kg), analogue 4Q was able to prevent thrombus formation in animals whose circulating platelet levels were one-third of normal. Analogue 4R at 10 mg/kg prevented occlusion throughout the duration of the study but at 3 mg/kg was ineffective.

In these studies, the degree of anti-thrombotic efficacy appeared to coincide with the anti-aggregation potency described above. For example, analogues 4Q and 4R, which were superior inhibitors of in vitro aggregation, also exerted a considerably greater in vivo protective effect than analogue 2G at the same injected concentration. Moreover, these peptides were able to prevent full occlusion only when they completely prevented platelet stimulation by all of the agonists (at 10 mg/kg). However, analogue 4Q (at 5 mg/kg) completely or near-maximally blocked all aggregation responses but could merely prolong coronary occlusion. In addition, analogue 4R at 3 mg/kg blocked aggregation responses by 72–100% at the three-and five-hour points, yet at these times an occlusive thrombus had fully developed. Finally, these peptides could completely prevent occlusion in this model only at injected concentrations equivalent to 20- to 50-fold greater than their $IC_{50}$s against in vitro aggregation.

Hemodynamic Responses

Bleeding time was quantified at 1 hour before and one, three, and five hours after administration of the peptide. This was done by making a small (5 mm long and 1.5 mm deep) incision in the tongue and subsequently absorbing the exuded blood at this site every 15 seconds with a piece of Whatman filter paper until bleeding stopped. Platelet counts were determined with a Haema Count MK-4/HC platelet counting system.

It is important to note that these apparently excessive peptide concentrations did not exert any significant effects on template bleeding time, platelet counts, or on the main hemodynamic parameters (heart rate and blood pressure), which remained essentially unchanged and similar to baseline values throughout the experimental periods (FIG. 5). In cases where peptide treatment did not prevent occlusion, at certain times these parameters were not determined (ND in Table II), as experiments were terminated 30 min. after circumflex coronary artery blood flow had ceased due to occlusive thrombus formation.

EXAMPLE VIII

Anti-Thrombotic Properties of Hydrophobically Enhanced RGd Peptides in Prostetic Arterial Grafts Adult male baboons (weighing 16 to 25 kg) were used in these studies. These were sedated with ketamine hydrochloride (200 to 250 mg intramuscular injection) and maintained under anesthesia with sodium pentobarbital (50 to 75 mg administered intravenously as necessary).

Twenty-four hours before the ex vivo shunt was established, platelets were isolated from 500 ml of blood from the test animal and labelled with ca. 500 microcuries of indium-111 oxine (Medi+Physics, Emeryville, Calif.), which irreversibly and specifically binds to platelets with an efficiency of 50%. Immediately after labelling, these platelets were then injected back into the animal and allowed to circulate for 24 hours. Immediately before the start of the study, fibrinogen that had been isolated from the animal and labelled with iodine-131 (DuPont Nuclear, Boston, Mass.) was also injected back into the animal. Also at this time, baseline determinations of the clotting and template bleeding times were made, and blood samples were drawn for hematology studies.

To establish the ex vivo shunt, the femoral artery and vein were percutaneously cannulated with introducer catheters (KMA Inc., Mansfield, Mass.). The catheters were then connected to medical-grade, heparin-coated silastic tubing (2.59 mm internal diameter, (Extracorporeal Medical Specialties, Inc., King of Prussia, Pa.). An electromagnetic flow probe was then inserted into the tubing by varying the resistance imparted by a partially occluding screw clamp that was distal to the probe. Finally, a 5 cm-long test segment of a 4 mm (internal diameter) vascular graft was inserted at the apex of the circuit. The graft used in these studies was Gore-tex (expanded polytetrafluoroethylene, (W. L. Gore and Associates, Inc., Flagstaff, Ariz.). An electromagnetic flow probe was then inserted into the tubing circuit to measure blood flow, which was maintained at 100 ml/min. by varying the resistance imported by a partially occluding screw clamp that was distal to the probe. Finally, a 5 cm-long test segment of a 4 mm (internal diameter) vascular graft was inserted at the apex of the circuit. The graft used in these studies was Gore-tex (expanded polytetrafluoroethylene, W. L. Gore and Associates, Inc., Flagstaff, Ariz.).

Platelet deposition onto the grafts was monitored by dynamic scanning with a gamma camera (Sigma 400, Ohio.

Nuclear, Inc., Sohon, Ohio), which detects the gamma radiation emitted by the indium$^{iii}$-labelled platelets. Once the circuit was in place, the animal was placed under this camera, and blood flow was initiated. Scans were then taken at the rate of one frame per two minutes for two hours. The data from these scans were collected on a dedicated Digital MDA computer (Maynard, Mass.). The scans were corrected for graft size, isotope dose and decay, circulating platelet activity and background, and the surface areas of the grafts.

At one- and two-hour time points, template bleeding times were measured, and blood samples were drawn to assess the hematology aggregation studies. Platelet aggregation studies were performed as described in Example V using ADP as the stimulus.

After a second, identical shunt was attached to the animal, the anti-platelet peptide GPenGHRGDLRCA was administered as an intravenous (IV) injection. A second series of scans was then obtained to ascertain the effect of the peptide on the platelet uptake pattern of the graft.

Upon the completion of each study, each shunt was flushed with Lactated Ringer's solution, and each graft was then removed. Sections of these grafts were subjected to liquid scintillation counting to determine their content of residual iodine$^{131}$-fibrinogen and indium$^{111}$-platelets. The catheters in the femoral artery and vein were then removed, and hemostasis was achieved by compression. Finally, postprocedural blood samples were drawn, and determinations of template bleeding and clotting times were also made.

Three different animals were used in order to account for animal variability. Two of the three test animals displayed normal platelet uptake patterns, as determined from gamma camera images of In$^{111}$-labeled platelets on the graft material. Treatments for these two animals are described below.

In the first of these animals, the peptide was administered as two bolus IV injections of 10 mg/kg (160 mg per injection). The first injection was given fifteen minutes before the establishment of the second shunt and the second injection was administered one hour afterward. As shown in FIG. 6, these injections caused a significant reduction in both In$^{111}$-platelet and I$^{131}$-fibrinogen uptakes (90% and 79%, respectively). This inhibitory effect is also apparent from a plot of platelet uptake rates in peptide-treated and untreated grafts over the entire time course of the studies (FIG. 7). Here, the rate of In$^{111}$-labelled platelet accumulation represents the counts observed in a graft piece minus those found in a background section of tubing at each time point when a scan was performed.

As shown in FIG. 8, peptide treatment did not lower template bleeding and clotting times. In blood samples taken immediately after completion of the second shunt, white blood cell and platelet counts, however, were reduced by 37% and 14%, respectively. Other parameters were unaffected.

Figure 9:
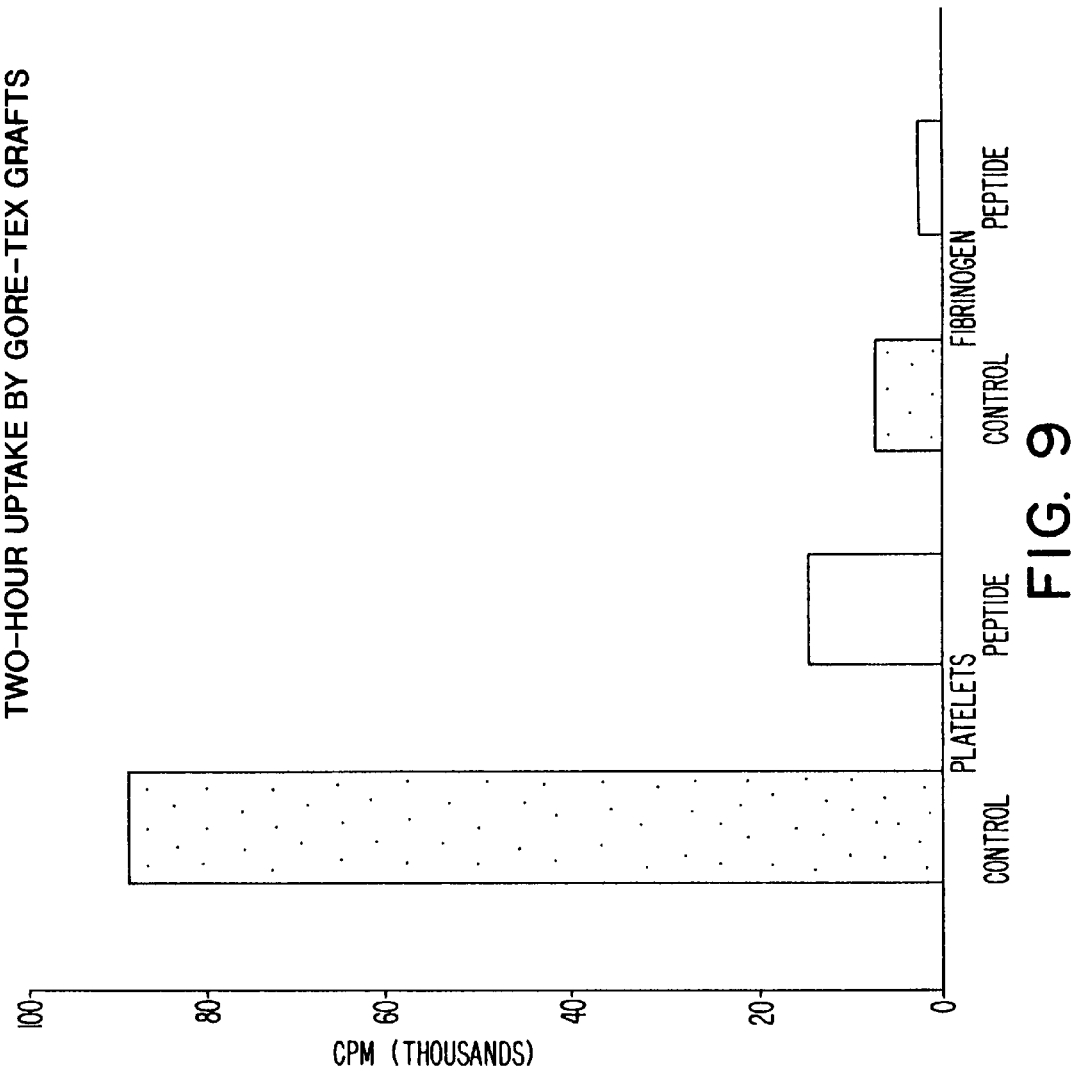
FIG. 9 shows the platelet and fibrinogen uptake by Gore-Tex grafts in animal 2 injected with the peptide of Example VIII.
Figure 10:
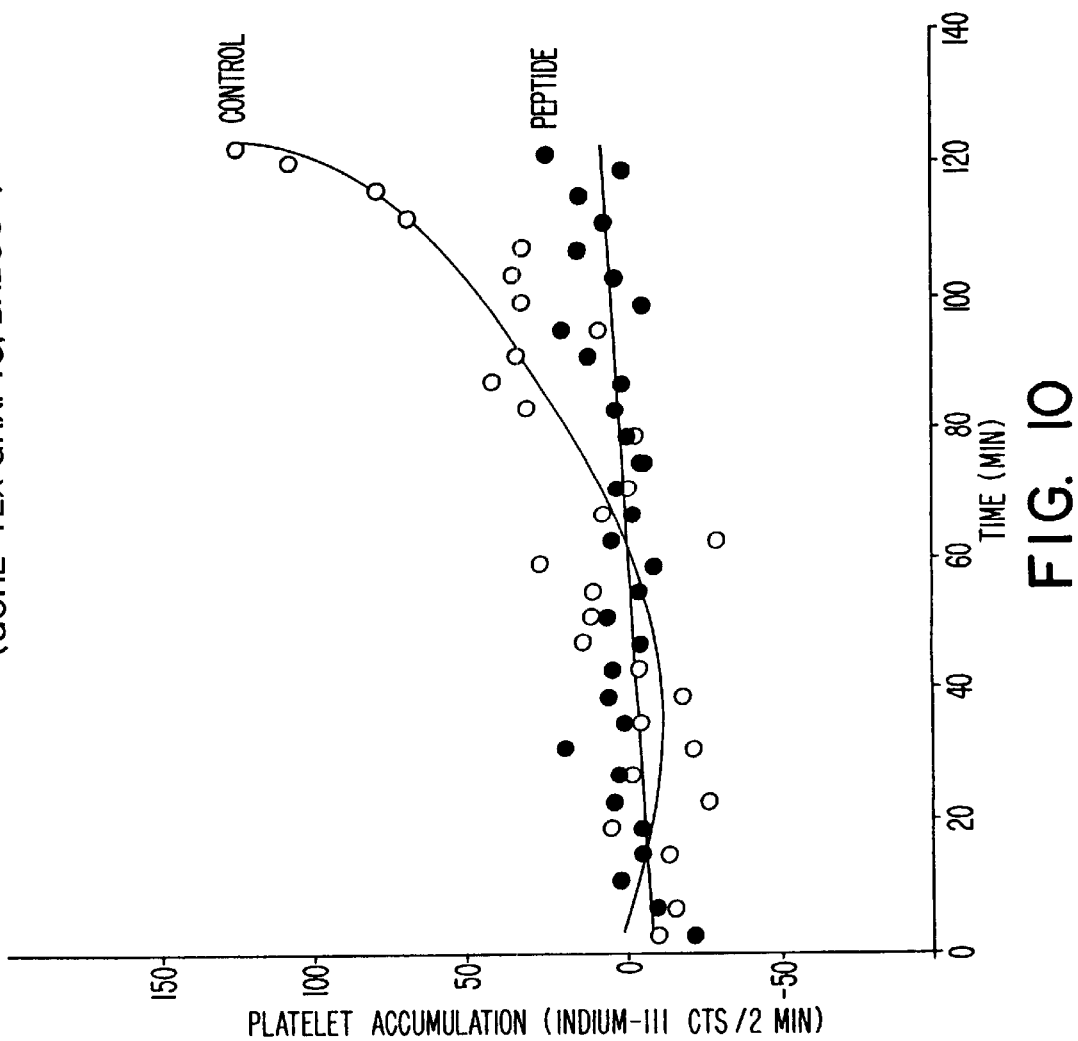
FIG. 10 shows the platelet uptake rates by Gore-Tex grafts in animal 2 injected with the peptide of Example VIII.

For the second animal, a 10 mg/kg bolus (250 mg) of the peptide was again given IV fifteen minutes before the initiation of the second shunt. This was immediately followed by a continuous infusion of 10 mg/kg/hr that lasted for the entire two hours of the shunt (500 mg total). As shown in FIG. 9, this treatment also caused significant reductions in labelled platelet and labelled fibrinogen uptakes (84% and 78%, respectively). Platelet uptake rates were again plotted in the presence and absence of the peptide (FIG. 10).

In addition, platelet aggregation studies were conducted on PRP derived from the second animal. Whole blood was drawn at three time points (0, 1 and 2 hours) of both control and experimental shunts. Platelets were completely unresponsive to the peptide treatment at a maximally effective concentration of ADP (10 μm). The peptide treatment also had no effect on template bleeding time, clotting time, or on all blood cell counts (FIG. 11).

We claim:

1. A composition of matter comprising a non-naturally occurring cyclic peptide having the sequence $X_2X_3X_4RGDX_1X_5X_6$ wherein $X_3$ and $X_5$ comprise moieties which form a bridge, $X_4$ is one or more amino acids, $X_2$ and $X_6$ are zero or more amino acids and $X_1$ is a hydrophobic moiety, said peptide exhibiting greater anti-thrombotic activity than a peptide containing a non-hydrophobic moiety in position $X_1$.

2. The composition of matter of claim 1 wherein $X_3$ and $X_5$ are selected from the group consisting of Cys, Pen, Pmp, and Pas.

3. The composition of claim 1 wherein $X_4$ has His as the carboxy terminal residue.

4. The composition of claim 1 wherein $X_2$ has Gly as the carboxy terminal residue.

5. The composition of matter of claim 1 wherein $X_1$ is selected from the group consisting of Phe, Tyr, PheCl, ChA and TyrMe.

6. The composition of matter of claim 1 wherein $X_1$ is TyrMe.

7. A peptide RPenGRGDWPCR.

8. The composition of matter of claim 1 in a physiological acceptable carrier.

9. The composition of matter of claim 1 wherein $X_3$ and $X_5$ are selected from the group consisting of Cys, Pen, Pmp and Pas and $X_1$ is selected from the group consisting of Phe, Val, Trp, Ile, Leu, TyrMe, PheCl and ChA.

10. A composition of matter comprising a non-naturally occurring cyclic peptide having the sequence $X_2X_3X_4RGDX_1X_5X_6$ wherein $X_3$ and $X_5$ comprise moieties which form a bridge, $X_4$ is one or more amino acids, $X_2$ and $X_6$ are zero or more amino acids and $X_1$ is a hydrophobic moiety selected from the group consisting of PheCl and ChA, said peptide exhibiting greater anti-thrombotic activity than a peptide containing a non-hydrophobic moiety in position $X_1$.

11. A method of treating thrombosis, comprising administering a therapeutically effective amount of the composition of claim 1 in a physiologically acceptable carrier.

12. A method of treating thrombosis, comprising administering a therapeutically effective amount of a peptide of claim 7 in a physiologically acceptable carrier.

* * * * *

UNITED STATES PATENT AND TRADEMARK OFFICE
CERTIFICATE OF CORRECTION

PATENT NO.    : 6,013,625
DATED         : January 11, 2000
INVENTOR(S)   : Pierschbacher et al.

It is certified that error appears in the above-identified patent and that said Letters Patent is hereby corrected as shown below:

Columns 9 and 10, Table I, second line from the bottom, please delete the values "28" and "0.64" (next to GHRGDLRPasA-NH$_2$) and replace with -- 4.8 -- and -- 3.2 --.

Signed and Sealed this

Second Day of September, 2003

JAMES E. ROGAN
*Director of the United States Patent and Trademark Office*